US012025581B2

(12) United States Patent
Weiss et al.

(10) Patent No.: US 12,025,581 B2
(45) Date of Patent: Jul. 2, 2024

(54) DEVICES AND METHODS FOR DETECTING/DISCRIMINATING COMPLEMENTARY AND MISMATCHED NUCLEIC ACIDS USING ULTRATHIN FILM FIELD-EFFECT TRANSISTORS

(71) Applicant: THE REGENTS OF THE UNIVERSITY OF CALIFORNIA, Oakland, CA (US)

(72) Inventors: Paul S. Weiss, Los Angeles, CA (US); Anne M. Andrews, Los Angeles, CA (US); Kevin M. Cheung, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 805 days.

(21) Appl. No.: 17/045,842

(22) PCT Filed: Apr. 11, 2019

(86) PCT No.: PCT/US2019/027080
§ 371 (c)(1),
(2) Date: Oct. 7, 2020

(87) PCT Pub. No.: WO2019/200164
PCT Pub. Date: Oct. 17, 2019

(65) Prior Publication Data
US 2021/0140917 A1    May 13, 2021

Related U.S. Application Data

(60) Provisional application No. 62/656,087, filed on Apr. 11, 2018.

(51) Int. Cl.
*G01N 27/414*    (2006.01)
*C12Q 1/6827*    (2018.01)

(52) U.S. Cl.
CPC ....... *G01N 27/4145* (2013.01); *C12Q 1/6827* (2013.01)

(58) Field of Classification Search
None
See application file for complete search history.

(56) References Cited

U.S. PATENT DOCUMENTS

| 2010/0297630 A1 | 11/2010 | Reijans et al. |
| 2011/0165557 A1 | 7/2011 | Ah et al. |

(Continued)

FOREIGN PATENT DOCUMENTS

WO    WO 2017/112941    6/2017

OTHER PUBLICATIONS

PCT International Search Report for PCT/US2019/027080, Applicant: The Regents of the University of California, Form PCT/ISA/210 and 220, dated Jun. 28, 2019 (3pages).

(Continued)

*Primary Examiner* — J. Christopher Ball
*Assistant Examiner* — John C Ball
(74) *Attorney, Agent, or Firm* — VISTA IP LAW GROUP LLP

(57) ABSTRACT

A method of detecting and/or discriminating mismatched or complementary nucleic acids using a field-effect transistor (FET). The FET comprises source and drain electrodes formed on substrate and separated by a channel that includes a thin semiconducting film. One or more nucleic acid molecules are immobilized to thin semiconducting film. The FET includes a gate electrode in contact with solution containing the sample (or located on the surface of the device). Samples possibly containing target nucleic acid are exposed to the FET of the biosensor device and current response is measured after samples containing target nucleic acid have been exposed to the FET of the biosensor device.

(Continued)

Measured current response in the FET is used to detect and/or discriminate whether target nucleic acid is present as well as complementary or mismatched. Measured current response may also be used to differentiate among different mismatches.

18 Claims, 14 Drawing Sheets

(56) References Cited

U.S. PATENT DOCUMENTS

| | | |
|---|---|---|
| 2011/0281288 A1 | 11/2011 | Chen et al. |
| 2014/0367255 A1 | 12/2014 | Samproni |
| 2015/0053966 A1 | 2/2015 | Steigner et al. |
| 2017/0059514 A1* | 3/2017 | Hoffman ............ G01N 33/5438 |

OTHER PUBLICATIONS

PCT Written Opinion of the International Search Authority for PPCT/US2019/027080, Applicant: The Regents of the University of California, Form PCT/ISA/237, dated Jun. 28, 2019 (11 pages).
Cai, B. et al., Ultrasensitive Label-Free Detection of PNADNA Hybridization by Reduced Graphene Oxide Field-Effect Transistor Biosensor, ACSNano, vol. 8, No. 3, 2632-2638, 2014.
Chen, H. et al., Quasi-Two-Dimensional Metal Oxide Semiconductors Based Ultrasensitive Potentiometric Biosensors, ACS Nano 2017, 11, 4710-4718, DOI: 10.1021/acsnano.7b00628.
Hwang, Michael T. et al., Highly specific SNP detection using 2D graphene electronics and DNA strand displacement, 7088-7093, PNAS, Jun. 28, 2016, vol. 113, No. 26, www.pnas.org/cgi/doi/10.1073/pnas.1603753113.
Kim, J. et al., Fabrication of High-Performance Ultrathin In2O3 Film Field-Effect Transistors and Biosensors Using Chemical Lift-Off Lithography, ACS Nano, vol. 9, No. 4, 4572-4582, 2015.
Lee, K-J et al., Single Nucleotide Polymorphism Detection Using Au-Decorated Single-Walled Carbon Nanotube Field Effect Transistors. Journal of Nanomaterials, vol. 2011, Article ID 105138, 8 pages, doi: 10.1155/2011/105138.
Liao, W-S et al., Subtractive Patterning via Chemical Lift-Off Lithography, Science 337, 1517-1521 (2012).
Nakatsuka, N et al., Aptamer-field-effect transistors overcome Debye length limitations for small-molecule sensing, Science. Oct. 19, 2018; 362(6412): 319-324. doi:10.1126/science.aao6750.
Ping, J. et al., Scalable Production of High-Sensitivity, Label-Free DNA Biosensors Based on Back-Gated Graphene Field Effect Transistors, ACS Nano 2016, 10, 8700-8704.
Rim, Y.S. et al., Printable Ultrathin Metal Oxide Semiconductor-Based Conformal Biosensors, ACS Nano, vol. 9, No. 12, 12174-12181, 2015.
Uno, T. et al., Peptide-Nucleic Acid-Modified Ion-Sensitive Field-Effect Transistor-Based Biosensor for Direct Detection of DNA Hybridization, Anal. Chem. 2007, 79, 52-59.
PCT International Preliminary Report on Patentability (Chapter I of the Patent Cooperation Treaty) for PCT/US2019/027080, Applicant: The Regents of the University of California, Form PCT/IB/326 and 373, dated Oct. 22, 2020 (13 pages).
The extended European search report dated Apr. 14, 2021, for European Patent Appl. No. 19785097.7, (10 pages).
Tonya M. Herne et al., Characterization of DNA Probes Immobilized on Gold Surfaces, J. Am. Chem. Soc. 1997, 119, 8916-8920.
Michael T. Hwang et al., Highly specific SNP detection using 2D graphene electronics and DNA strand displacement, PNAS, Jun. 28, 2016, vol. 113, No. 26, 7088-7093.
Bingjie Cai et al., Ultrasensitive Label-Free Detection of PNA-DNA Hybridization by Reduced Graphene Oxide Field-Effect Transistor Biosensor, ACSNano, vol. 8, No. 3, 2632-2638 (2014).
Jaemyung Kim et al., Fabrication of High-Performance Ultrathin In2O3 Film Field-Effect Transistors and Biosensors Using Chemical Lift-Off Lithography, ACSNano, vol. 9, No. 4, 4572-4582, (2015).
Response to extended European search report dated Nov. 15, 2021, for European Patent Appl. No. 19785097.7, (63 pages).
Communication pursuant to Article 94(3) EPC dated Jul. 18, 2023 for European Patent Appl No. 19785097.7, (7 pages).
D. Goncalves et al., Detection of DNA and proteins using amorphous silicon ion-sensitive thin-film field effect transistors, Biosensors and Bioelectronics 24 (2008) 545-551.
Reply to communication pursuant to Article 94(3) EPC, First Examination Report, dated Jan. 29, 2024, for European Patent Application No. 19785097.7, (64 pages).

\* cited by examiner

FIG. 2A ssDNA-functionalized FET

FIG. 2B Hybridization with complementary DNA/RNA sequence (161)

FIG. 2C Detection of DNA/RNA with single-base mismatches (162)

FIG. 2D Non-Complementary DNA/RNA control (163)

140 Thiolated: HS-GGT TGT TGG C̲TA TAA
142c Complementary: CCA ACA ACC GAT ATT
142m Mismatch: CCA ACA ACC C̲AT ATT 140 Thiolated: HS-GGT TGT TGG ATA TAC̲
142c Complementary: CCA ACA ACC TAT ATG
142m Mismatch: CCA ACA ACC TAT ATC̲

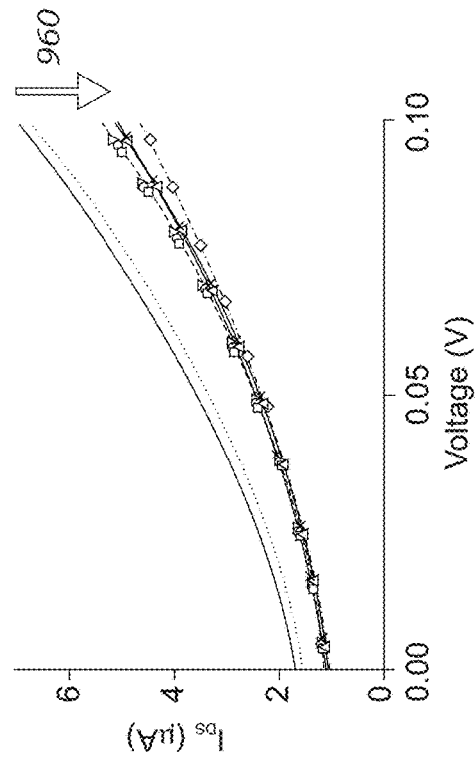
FIG. 9E
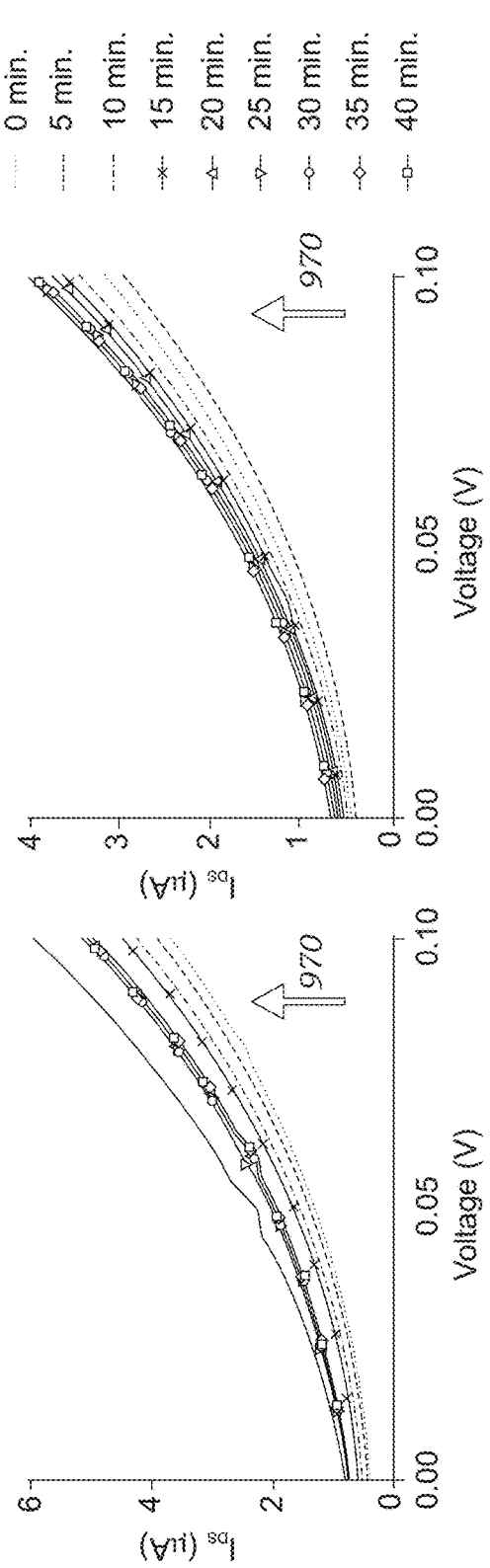
FIG. 9F
FIG. 9G

DEVICES AND METHODS FOR DETECTING/DISCRIMINATING COMPLEMENTARY AND MISMATCHED NUCLEIC ACIDS USING ULTRATHIN FILM FIELD-EFFECT TRANSISTORS

CROSS-REFERENCE TO RELATED APPLICATION

This application is a U.S. National Stage filing under 35 U.S.C. § 371 of International Application No. PCT/US2019/027080, filed Apr. 11, 2019, which claims priority under 35 U.S.C. § 119 of U.S. Provisional Application No. 62/656,087, filed Apr. 11, 2018, and entitled DEVICES AND METHODS FOR DETECTING/DISCRIMINATING COMPLEMENTARY AND MISMATCHED NUCLEIC ACIDS USING ULTRATHIN FILM FIELD-EFFECT TRANSISTORS, the contents of which are incorporated herein by reference as though set forth in full. Priority is claimed pursuant to 35 U.S.C. §§ 119, 371 and any other applicable statute.

STATEMENT REGARDING FEDERALLY SPONSORED RESEARCH AND DEVELOPMENT

This invention was made with government support under DA045550, awarded by the National Institutes of Health. The government has certain rights in the invention.

TECHNICAL FIELD

The technical field generally relates to biosensors used to detect complementary and mismatched nucleic acids including single nucleotide polymorphisms (SNPs).

BACKGROUND

There is a need to detect complementary and mismatched nucleic acids. For example, SNPs are a common variation in the DNA sequence of organisms where a single base pair or nucleotide is mismatched. The current gold standard techniques used for SNP detection utilize polymerase chain reaction-based methods or fluorophore-modified nucleic acid sequences. Both of these methods either require amplification of the nucleic sequences of interest or indirect detection via fluorescent probes or both. These are time-consuming assays that require reagents for amplification and detection and need laboratory-scale environments to perform the required operations.

Various attempts have been made to use field effect transistor (FET) based biosensors to detect SNPs. Such biosensor-based FETs are gated by changes in the surface potential induced by the binding of charged molecules to the FET gate. In a typical FET device, a semiconducting layer is used as the underlying channel material along with metallic source and drain electrodes. An insulating layer such as silicon dioxide is used to separate the semiconducting channel material from the underlying substrate. A molecular layer, commonly a molecular monolayer, is typically formed on the oxide layer and has receptor molecules bound thereto. Upon binding of the analyte to the receptor molecules, changes in the electrostatic potential at the surface of the FET device result in an electrostatic gating effect of the semiconductor device and a measurable change in current between the source and drain electrodes.

More recently, graphene-based FET biosensors have been disclosed for the detection of nucleic acid hybridization including high-specificity, single nucleotide mismatch detection. Others have looked at nanotube-based FET devices to detect nucleic acids. Unfortunately, these materials are complicated in that reproducible production and chemical functionalization are highly challenging. Previous FET-based biosensors have also suffered from other shortcomings including low sensitivity, particularly with physiological fluids or low throughput.

SUMMARY

Embodiments relate to biosensors able to detect whether a target sequence or nucleic acid is complementary, a mismatch or non-complementary relative to a nucleic acid molecule or sequence immobilized to a channel of a thin semiconductor layer of a field-effect transistor (FET) based on the FET current response or current shift. In some embodiments, the FET-based biosensor is able to discriminate between different types of mismatches.

Embodiments are also related to label-free target nucleic acid detection and discrimination including detection of single nucleic acid mismatches and discrimination of different sequence mismatches.

Embodiments are also related to semiconductor biosensor devices and biosensing systems and current responses of semiconductor devices to determine whether a target nucleic acid is complementary, a mismatch or non-complimentary relative to a nucleic acid molecule or sequence immobilized or linked to a semiconductor layer of a FET.

A method of detecting and/or discriminating mismatched or complementary nucleic acids using a FET-based biosensor device is disclosed. The biosensor device has one or more FETs disposed on a substrate. Each FET includes a source electrode and a drain electrode formed on the substrate and separated by a channel formed as a thin semiconducting film. One or more nucleic acid molecules are immobilized to the thin semiconducting film. The FET includes a gate electrode that, in one embodiment, is in contact with a solution containing the sample to be analyzed. A reference electrode (e.g., silver/silver chloride reference electrode) can also optionally be used as the gate electrode. In alternative embodiments, the gate electrode may be disposed on the surface of the biosensor device (e.g., solid state reference electrode). Samples containing target nucleic acid are exposed to the FET of the biosensor device and the current response is measured using a parameter analyzer or other device after the samples containing the suspected target nucleic acid have been exposed to the FET of the biosensor device. The measured current response of the FET is used to detect and/or discriminate target nucleic acid, e.g., whether the target nucleic acid is present and if it is complementary or mismatched or discriminating mismatched target nucleic acids. The FET may also be used to identify types of mismatches that are present. A multiplicity of FETs working in concert can be used in concert to identify the mismatches more precisely. Multiple FETs may also be used to perform multiplex testing on different target nucleic acids. The method may be employed with target DNA, RNA, or other nucleic acids (e.g., morpholinos).

One embodiment is for a FET-based method for detecting and/or discriminating mismatched or complementary nucleic acids. The method comprises providing a biosensor device comprising having a FET disposed on a substrate. The FET includes a gate electrode, a source electrode disposed on the substrate, a drain electrode disposed on the substrate and a thin semiconducting film forming a channel between the source electrode and drain electrode. A nucleic acid molecule or sequence is immobilized to the channel formed by the thin semiconducting film. A sample containing a target nucleic acid is exposed or applied to the FET and the FET's current response is measured after the sample has been exposed or applied to the FET. The method further comprises detecting and/or discriminating whether the target nucleic acid is complementary or mismatched with the immobilized nucleic acid molecule or sequence based on the FET's measured current response.

Another embodiment is for a method of discriminating between single nucleotide mismatches in a nucleic acid using a FET device. The method comprises providing a biosensor device comprising having a FET disposed on a substrate, the FET including a gate electrode, source and drain electrodes disposed on the substrate, a thin semiconducting film forming a channel between the source electrode and drain electrode, and a nucleic acid molecule or sequence immobilized to the channel. The method further comprises exposing or applying a sample containing a target nucleic acid having single nucleotide mismatches to the FET of the biosensor device, measuring the current response in the FET after the samples have been exposed or applied to the FET of the biosensor device and discriminating the samples based on the measured current response in the FET.

A further embodiment is for a biosensor device operable or configured to detect and/or discriminate mismatched or complementary nucleic acids using a FET and FET current responses. One embodiment of a biosensor device is in the form of a FET device that includes a substrate, a gate electrode, source and drain electrodes disposed on the substrate, and a thin semiconducting film forming a channel between the source and drain electrodes. The source electrode and the drain electrode are configured so that an electric current flows between the source electrode and the drain electrode and through the channel in response to a voltage applied to the gate electrode. A nucleic acid molecule or sequence is indirectly immobilized to the channel through an intermediate linking element. One example of an intermediate linking element utilized is embodiments is a combination of (3-aminopropyl) trimethoxysilane (APTMS) and 3-maleimidobenzoic acid N-hydroxysuccinimide ester (MBS). The nucleic acid or immobilized sequence (e.g., when thiolated) binds to the MBS component of the intermediate linking element, and the APTMS component of the intermediate linking element binds to a thin semiconductor layer channel of FET. Passive or inactive spacer elements, such as trimethoxy(propyl)silane (PTMS) elements, are laterally disposed between respective linking elements to separate respective linking elements and respective nucleic acid molecules or target sequences attached to respective linking elements. Nucleic acid molecules are not attached to a passive spacer element. The degree of spacing between immobilized nucleic acids that are indirectly bound to the thin semiconductor layer channel of the FET may be controlled by adjusting the relative amounts of PTMS/APTMS during the deposition of the same during the manufacturing process.

Further embodiments are for a biosensing system configured to execute method embodiments and which may include a biosensor device, a semiconductor parameter analyzer coupled to the biosensor device to detect current responses thereof, and a computing device. The computing device is in communication with the semiconductor parameter analyzer to receive the current response output generated by the semiconductor parameter analyzer. The computing device identifies whether a sample with a target nucleic acid exposed or applied to the FET is complementary or mismatched with the immobilized nucleic acid molecule tethered to a thin semiconductor layer of the FET.

In a single embodiment or multiple embodiments, a nucleic acid molecule that is immobilized to the thin semiconducting film channel may include deoxyribonucleic acid (DNA), ribonucleic acid (RNA), and/or such molecules that include unnatural nucleic acids that are effectively complementary to more than one natural base (so-called wild card bases). The sample exposed or applied to the FET may be a sample containing a target nucleic acid include a single nucleotide polymorphism with the one or more nucleic acid molecules and that may include DNA or RNA. The target nucleic acid of the sample exposed or applied to the FET can be present in the sample even at a femtomolar concentration ranges or smaller. The sample may be a non-diluted physiological sample such as blood or saliva or other fluids, may be from fixed tissue samples, or the sample may be diluted with a buffer solution.

In a single embodiment or multiple embodiments, the thin semiconducting film comprises a layer a semiconductor metal oxide, namely indium oxide ($In_2O_3$), which may have a thickness less than about 5 nm. The thin semiconducting layer may form a channel structured as interdigitated array of interleaved fingers.

In a single embodiment or multiple embodiments, at least one nucleic acid molecule or sequence is indirectly immobilized to the channel formed by the thin semiconducting film by an intermediate linking element. The intermediate linking element is attached between the channel and the nucleic acid molecule or immobilization sequence. The intermediate linking element may include multiple linking components. In one embodiment, a first linking component binds or is attached to the channel, and a second linking component binds or is attached to the first linking component such that at least one nucleic acid or sequence is indirectly immobilized to the channel. For example, the first linking component may be (3-aminopropyl)trimethoxysilane (APTMS), and the second linking component may be 3-maleimidobenzoic acid N-hydroxysuccinimide ester (MBS). The nucleic acid molecule or sequence may be thiolated to bind to the second linking component to indirectly immobilize the nucleic acid molecule to the channel.

In a single embodiment or multiple embodiments, passive or non-reactive spacer elements, e.g., PTMS elements, are attached to the channel and are laterally disposed between respective intermediate linking elements to separate respective linking elements. Respective nucleic acid molecules are not attached to the passive spacer elements. The combination of the intermediate linking element and spacer elements and ratios of the active component APTMS to PTMS provides for APTMS being deposited in moderation so that excessive target nucleic acid molecules are not tethered to respective immobilized nucleic acid molecules, which may sterically interfere with one another and/or alter current responses and determinations based on same. According to one embodiment, the ratio of intermediate linking element to passive spacer element during the deposition process is less than about 1:9.

In a single embodiment or multiple embodiments, the FET current response is measured by measuring a current between the source electrode and the drain electrode when the sample containing the target nucleic acid is exposed or applied to the FET. The FET's current response is measured after exposing the one or more samples containing target nucleic acid to the FET of the biosensor and sweeping a voltage applied to the gate electrode of the FET from a first voltage to a second voltage over a pre-determined time. For example, the voltage applied to the gate electrode is swept from 0 mV to about 400 mV in 5 mV steps during a sweep time that lasts several seconds (e.g., 4-5 seconds) and typically less than 10 seconds. Additional measurements are made as time progresses (e.g., every 5 minutes or so) with current shifts typically being observed between about 30 and 60 minutes after sample addition. Typically, at least 20 minutes or so after sample addition is a sufficient amount of time to allow the FET current response to indicate whether a target nucleic acid or sequence in a specimen or sample is complementary, a mismatch or non-complementary relative to a nucleic acid immobilized to the thin semiconductor material of the FET. The current response may involve a current shift between a first current between the source electrode and the drain electrode resulting from exposing a sample free of the target nucleic acid to the FET, and a second current between the source electrode and the drain electrode resulting from exposing the sample containing the target nucleic acid to the FET. Embodiments may involve a biosensor device including one or multiple FETs, which may include one or multiple different immobilized nucleic acid molecules.

In a single embodiment or multiple embodiments, a FET is coupled to a semiconductor parameter analyzer, which measures the FET current response after the one or more samples have been exposed or applied to the FET. In some embodiments, a computing device may receive the semiconductor parameter analyzer output to identify a transconductance change, e.g., whether current responses fit certain current responses or current changes such as a shift of source drain current in response to gate electrode voltage changes, in order to determine whether the sample includes a target nucleic acid that is complementary or mismatched. For these purposes, the semiconductor parameter analyzer maintains a constant voltage at the source electrode and the drain electrode and sweeps a gate electrode voltage from a first gate voltage to a second gate voltage. Alternatively, the output functionality of the computing device may be integrated into the semiconductor parameter analyzer.

In a single embodiment or multiple embodiments, a wall or cup layer is deposited or otherwise formed to extend upwardly from the source electrode and the drain electrode to define a well. The well contains a sample solution to allow the sample to be applied to the FET for analysis.

In a single embodiment or multiple embodiments, a mismatch of a single nucleotide base pair between a first nucleotide base of the immobilized nucleic acid molecule and a second nucleotide base of the target molecule is detected based at least in part upon the measured current response of a FET structured according to embodiments. The measured current response may also be used to identify samples containing target nucleic acids that are complementary to an immobilized one (e.g., containing complementary A-T and G-C base pairs), and to identify different nucleotide base pair mismatches (e.g., a C-C base pair mismatch, a C-T base pair mismatch and a C-A base pair mismatch). Embodiments are able to identify a single nucleotide base that does not match a corresponding nucleotide base of the immobilized nucleic acid or sequence based at least in part upon the measured current response of the FET. In other embodiments, the measured current response may be used to distinguish the type or nature of the mismatch between the target nucleic acid sequence and the immobilized nucleic acid sequence.

BRIEF DESCRIPTION OF THE DRAWINGS

FIG. 2A depicts a FET device constructed according to one embodiment including a thin film of an indium oxide semiconducting layer disposed between source and drain electrodes, and FIGS. 2B-2D schematically illustrate how the FET device may be used or hybridized with complementary, mismatched (including single-base mismatch), and noncomplementary target DNA or RNA sequences;

FIGS. 7A-7C illustrates FET configurations and exemplary dimensions according to various embodiments, wherein FIG. 7A illustrates an optical micrograph of a FET structured to one embodiment, FIG. 7B illustrates a schematic of a FET illustrating illustrative channel dimensions according to certain embodiments, and FIG. 7C illustrates a scanning electron microscope image of a representative FET device including gold source and drain electrodes and indium oxide channels;

FIGS. 9A-9G illustrate examples of FET current responses of FETs structured according to embodiments, wherein FIG. 9A is a graph of mean FET responses after 30 minutes of target DNA incubation and shows how FET devices structured according to embodiments can be used to detect and discriminate single DNA base pair mismatches from fully complementary sequences, non-complementary sequences, and sequences with different types of mismatches, FIG. 9B illustrates DNA sequences used for experiments shown in FIG. 9A, FIG. 9C is a graph of the normalized mean FET responses after 30 minutes of target DNA incubation and shows how FET device configured according to embodiments can be used to detect C-C mismatches on DNA sequences certain bases away from their thiolate attachments, FIG. 9D illustrates the DNA sequences used for experiments shown in FIG. 9C, and FIGS. 9E-9F demonstrate how representative transfer characteristics or I-V curves of DNA functionalized FETs of embodiments over time upon exposure to a fully complementary sequence, a non-complementary sequence, and a mismatched sequence respectively and demonstrate that curves for complementary sequences show a stable decrease in current over time, whereas curves for non-complementary and mismatched sequences shift back towards the baseline current over time;

DETAILED DESCRIPTION OF ILLUSTRATED EMBODIMENTS

Figure 1:
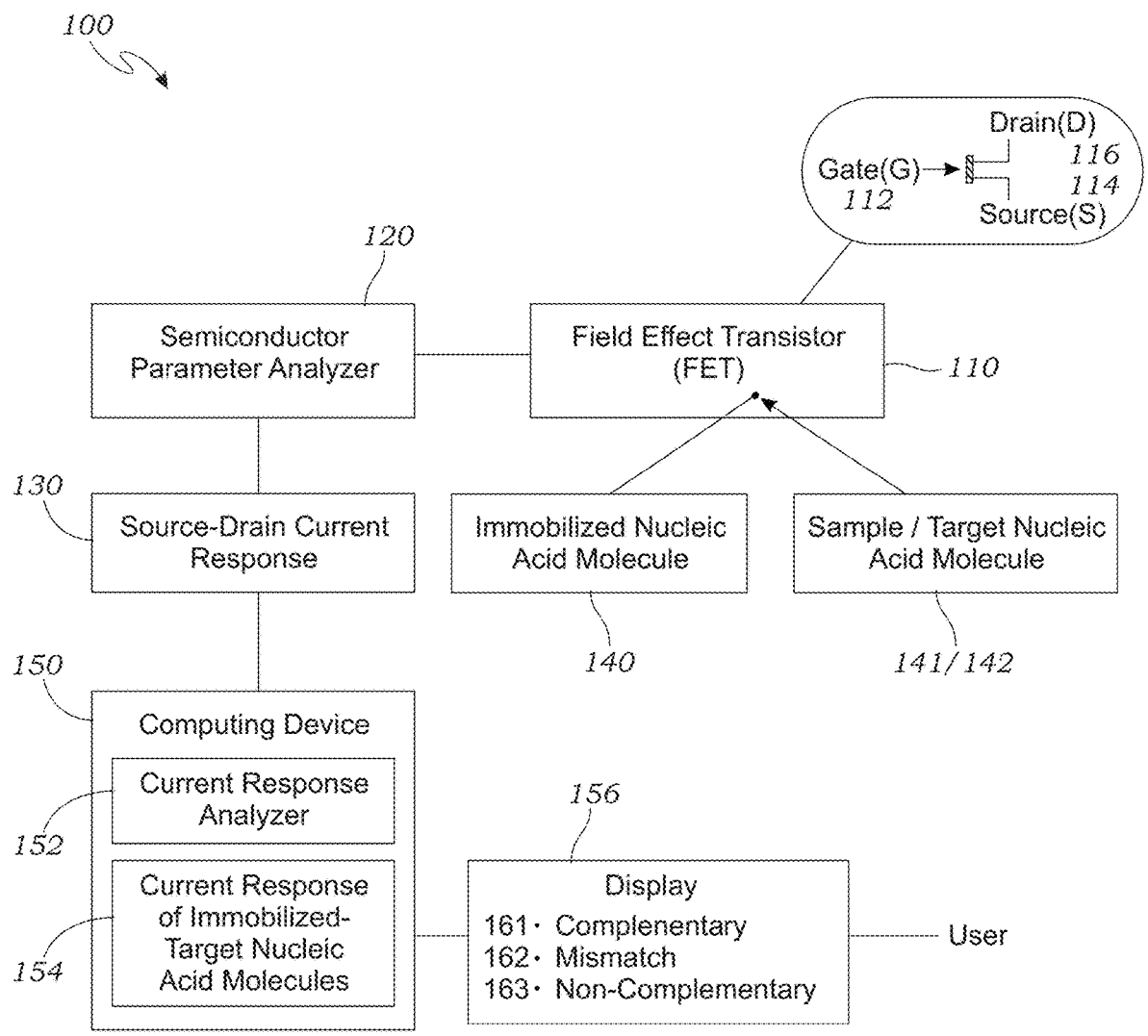
FIG. 1 is a block diagram of a biosensing system constructed according to one embodiment and including a FET designed according to one embodiment for target nucleic acid detection and/or discrimination.
Figure 2:
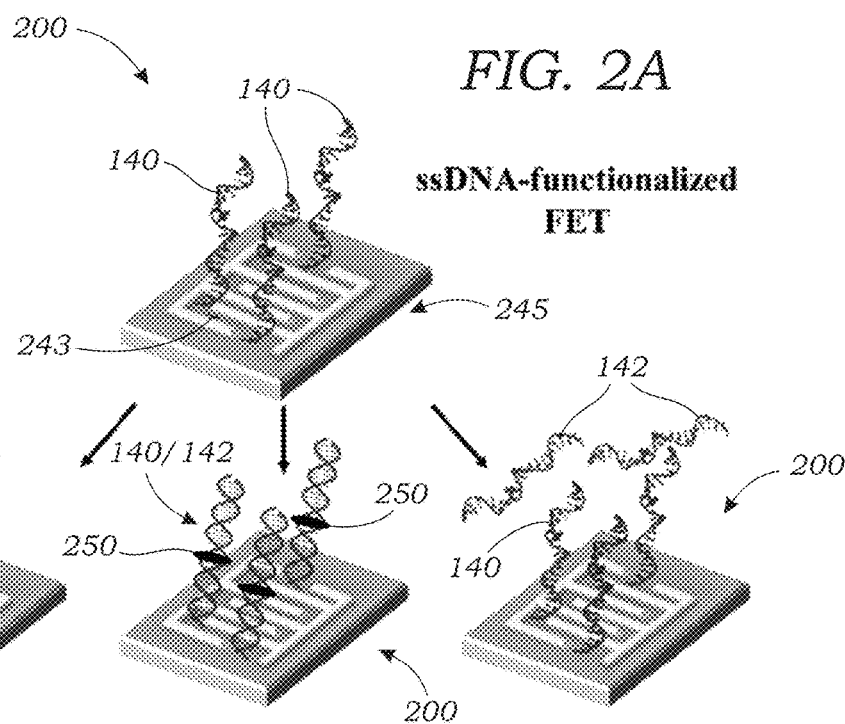
FIGS. 2A-2D schematically illustrate different modes of using the FET device.

Embodiments of the invention provide for computerized and automated methods, transistor devices and biosensor systems able to detect whether a target nucleic acid molecule or sequence (e.g., a DNA molecule) is complementary, a mismatch or non-complementary relative to a nucleic acid molecule or sequence (e.g., immobilized DNA molecule) that has been chemically tethered or immobilized to a portion of the transistor device. Methods and devices of embodiments may also be used to discriminate different types of nucleic mismatches between the immobilized nucleic acid and the target nucleic acid. These detections are based on how current flow through the transistor device changes as different voltages are applied or swept to certain portions of the transistor device. Embodiments thus provide for label-free target nucleic acid or sequence detection and also discrimination among target nucleic acid molecules or sequences (e.g., among target nucleic acid molecules that do not match a tethered or immobilized nucleic acid molecule).

DNA molecules are comprised of four building blocks, bases or nucleotides: cytosine (C), thymine (T), adenine (A), and guanine (G). DNA strands are structured so that certain base pairs are properly bound to each other, also referred to as Watson-Crick base pairs. More specifically, a proper, matching base pair is formed by bonding of guanine (G) and cytosine (C), and another proper, matching base pair is formed by bonding of adenine (A) and thymine (T). These nucleotide structures form the basis of the DNA double helix.

Detection and discrimination capabilities provided by embodiments allow functionalized transistor-based sensor devices to distinguish between different types, locations, and numbers DNA polymorphisms, or differences in these nucleotide or base pairings. These polymorphisms or differences may involve a base pair change, insertion or deletion and may result from and be indicative of various diseases or medical conditions or predispositions to diseases or medical conditions such as cancer. Examples of DNA polymorphisms may be a mismatch caused by formation of an adenine (A) and cytosine (C) pair (rather than proper A-T and C-G pairings).

Embodiments may also be utilized to tether or immobilize RNA or DNA molecules to a FET semiconductor channel and to detect target RNA 142. RNA molecules are similar to their DNA counterparts except that they contain the sugar ribose, without the hydroxyl modifications of deoxyribose that is found in DNA. In addition, RNA replaces the thymine base (T) with uracil (U). Artificial bases can be employed that are complementary to more than one natural base and used for more efficient analyses of the presence of collections of sequences and/or the location of one or more mismatches.

Embodiments of the invention provide for detection of nucleotide polymorphisms, and even a single nucleotide polymorphism of a single mismatched base pair and may involve a biological fluid such as blood, urine, saliva, or the like, and which may be a non-diluted physiological sample or diluted with an appropriate buffer solution or water.

Embodiments may be used for improved and more efficient and accurate disease diagnostics, precision medicine including point-of-care, oncology and pathology applications and genetic mapping applications. Further aspects of how embodiments of the invention are structured, fabricated, functionalized and executed are described with reference to FIGS. 1-11B.

Referring to FIG. 1, a biosensor system 100 constructed according to one embodiment includes a biosensor device in the form of a field effect transistor (FET) 110 that is fabricated and functionalized in particular ways for improved biosensing according to embodiments. FET 110 is a three terminal "voltage controlled" transistor device that includes a gate (G) electrode 112, a source (S) electrode 114 and a drain (D) electrode 116. Gate electrode 112 is a terminal that modulates the conductivity or flow of current through a conductive semiconductor channel defined between source electrode 114 and drain electrode 116. In other words, flow of current between source electrode 114 and drain electrode 116 is controllably adjustable by changing the voltage applied to gate electrode 112.

Embodiments may involve various types of FETs 110 that provide for voltage-controlled current flow including junction gate field-effect transistors (JFETs) and metal oxide semiconductor field effect transistors (MOSFETs). Embodiments may also involve different channel variations thereof including n-channel and p-channel JFETs and MOSFETs. Embodiments may also involve FETs that operate in different modes including enhancement mode and depletion mode. For ease of explanation and not limitation, reference is made generally to FET 110 and to gate electrode 112, source electrode 114 and drain electrode 116 of FET 110.

In the illustrated embodiment, biosensor system 100 includes a semiconductor parameter analyzer 120 (generally, analyzer 120) coupled to FET 110—coupled to gate electrode 112, source electrode 114 and drain electrode 116 of FET 110. Analyzer 120 is a computerized test instrument that measures FET's electrical parameters such as transconductance or a FETs current response 130 over time as voltage applied to gate electrode 112 changes. One example of analyzer 120 that may be utilized in embodiments is Keithley 4200A-SCS parameter analyzer 120 available from Tektronix, Inc., Beaverton, OR According to embodiments, a change of current flowing between source electrode 114 and drain electrode 116 based on changing voltage applied to gate electrode 112 while voltages on source and drain electrodes 114, 116 remain the same. For ease of explanation, reference is made generally to analyzer 120 and measured current response 130 between source electrode 114 and drain electrode 116 of FET 110.

Current response 130 of FET 110 is monitored by analyzer 120 based on hybridization or the interaction between an immobilized nucleic acid molecule or sequence 140 (generally, immobilized molecule or immobilized sequence 140) and a target nucleic acid molecule or sequence 142 (generally, target molecule or target sequence 142) of a sample 141 that is being analyzed using functionalized FET 100. Immobilized sequence 140 is tethered to a portion of FET 110 to functionalize FET 110, and in particular, to a semiconductor channel region 243 of the FET 110. Current response 130 (e.g., current shift) of FET 110 changes are based on whether nucleotides or base pairs of immobilized sequence 140 and target sequence 142 match, do not match, or are not complementary such that they may not bond together. In other words, as target sequence 142 components bind (whether matching or not), these interactions or hybridizations result in corresponding changes to FET 110 current over time and with different applied gate electrode 112 voltages, which are measured by analyzer 120. Analyzer 120 measurements are received, in some embodiments, by a computing device 150 that includes a current response analyzer 152 that generates a current response of immobilized target nucleic acids 154, for example, relative to a database of known current responses or baselines without addition of any nucleic acids. Results of whether target nucleic acid molecule(s) 142 is/are complementary 161, a mismatch 162 (even a single mismatched pair) or non-complementary 163, and type(s) of mismatch 162 are presented to a user of biosensor system 100 through a display 156 of computing device 150.

For example, with further reference to FIGS. 2A-2D, a FET-based biosensor device 200 constructed according to one embodiment includes FET 110 formed on a substrate 245 (generally depicted in FIGS. 2A-2D). FET 110 is functionalized with immobilized sequence 140 in the form of a single-stranded DNA (ssDNA). The ssDNA functionalization element or immobilized sequence 140 (generally illustrated as "half" of a "double helix" in FIG. 2A) is tethered or linked to a semiconductor channel region 243 (generally, channel 243) of FET 110. FET 110 operates in three different modes or is operable to detect three different states due to interactions of immobilized sequence 140 and target sequence 142.

FET 110 may operate in a first or "complementary" mode 161 generally depicted in FIG. 2B. In this mode, FET 110 is hybridized with complementary DNA or RNA. In other words, bases or nucleotides of target sequence 142 properly link and match up with corresponding bases or nucleotides of immobilized sequence 140 (e.g., proper A-T and proper C-G matches). This "complementary" hybridization has a certain current response 130.

FET 110 may operate in a second "mismatch" mode 162 (generally depicted in FIG. 2C). In this mode, FET 110 is hybridized with DNA or RNA that contains one or more base mismatches 250. For example, rather than a proper G-C pair, a mismatch 250 may be C-A, C-T and C-C. As another example, rather than a proper A-T pair, a mismatch may be A-C, A-G and A-A. Each "mismatch" 250 hybridization has a certain current response 130 and mismatch hybridization may involve a single mismatch or multiple mismatches 250. As explained herein, in some embodiments, the particular type or nature of the mismatch may be detected by the FET 110. For example, the measured current response may be used to distinguish or identify a CC mismatch from a CA mismatch or a CT mismatch (seen, for example, in FIG. 11A).

A third "non-complementary" mode 163 is generally depicted in FIG. 2D. As depicted in FIG. 2D, immobilized sequence 140 may not link with target sequence 142 due to target sequence 142 being non-complementary DNA or RNA, meaning that target sequence 142 may not even bond with immobilized sequence 140 or does so to a substantially limited extent given multiple mismatches 250 or different molecule structures so as to be effectively disjointed or only be capable of limited hybridization.

Figure 3:
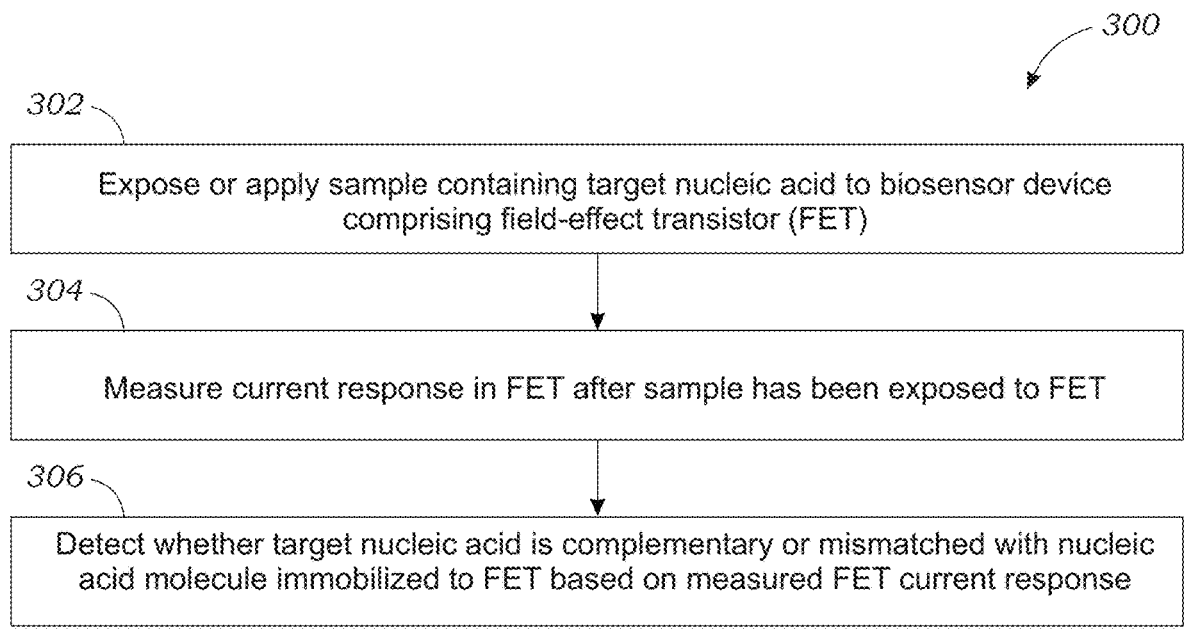
FIG. 3 is a flow diagram of one embodiment of FET-based target nucleic acid molecular detection.

With continuing reference to FIGS. 1 and 2A-2D, and with further reference to FIG. 3, one embodiment of a method 300 involves, at 302, exposing or applying sample 141 containing target sequence 142 to biosensor device including FET 110 functionalized with immobilized sequence 140. At 304, analyzer 120 measures current response 130 of FET 110 after sample 141 has been exposed or applied to FET 110. At 306, biosensor system detects whether target sequence 142 hybridized to immobilized sequence 140 is complementary or mismatched (or non-complementary) based on measured FET current response 130.

Figure 4:
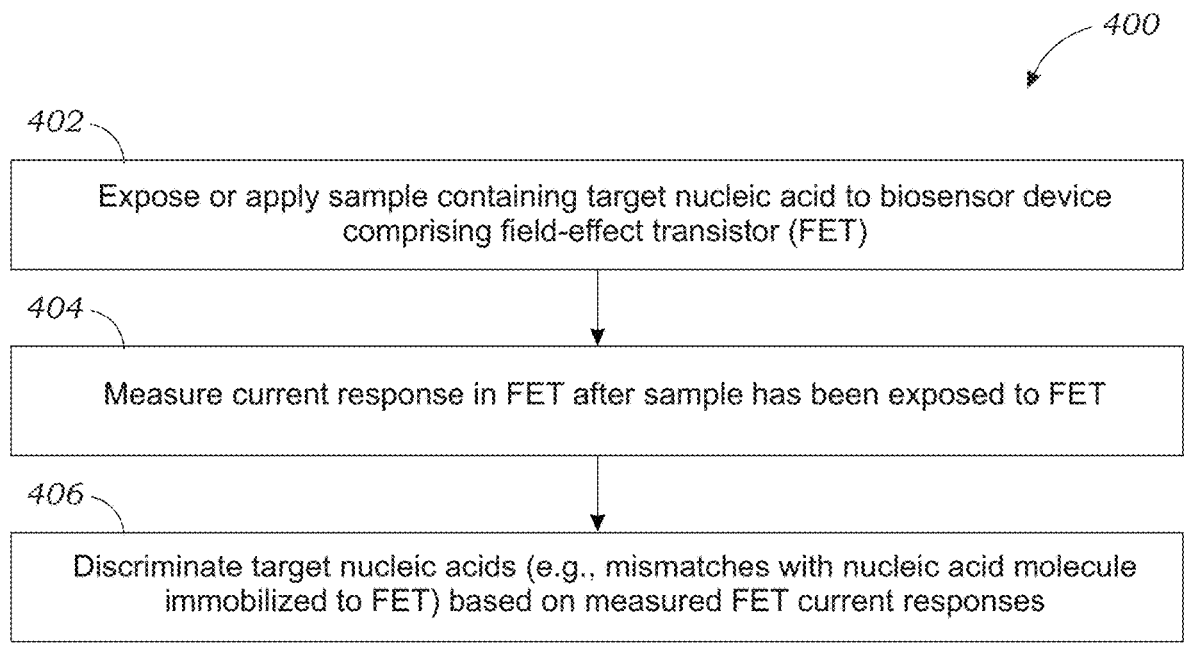
FIG. 4 is a flow diagram of one embodiment of FET-based target nucleic acid molecule discrimination.

With continuing reference to FIGS. 1 and 2A-2D, and with further reference to FIG. 4, another embodiment of a method 400 is utilized to not only detect target sequences hybridized with immobilized sequence 140, but also discriminate or distinguish target sequences 142, e.g., distinguish different target sequence mismatches 250. One embodiment involves, at 402, exposing or applying sample 141 containing target sequence 142 to biosensor device including FET 110 functionalized with immobilized sequence 140. At 404, analyzer 120 measures current response 130 of FET 110 after sample 141 has been exposed or applied to FET 110. At 406, biosensor system discriminates or distinguishes target nucleic acid molecules 142 such as different mismatching target sequences or mismatching base pairs thereof based on measured FET current responses 130.

Figure 5:
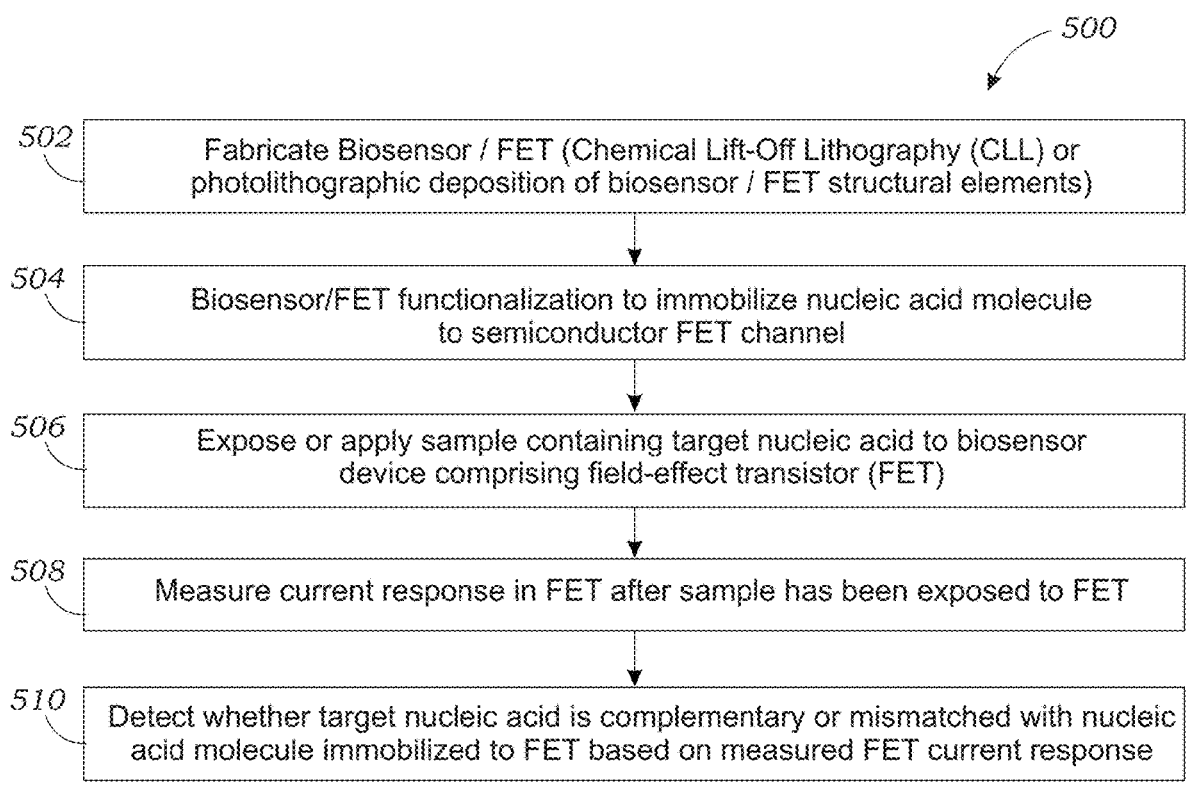
FIG. 5 is a flow diagram of a further embodiment of FET-based target nucleic acid molecular detection.
Figure 6:
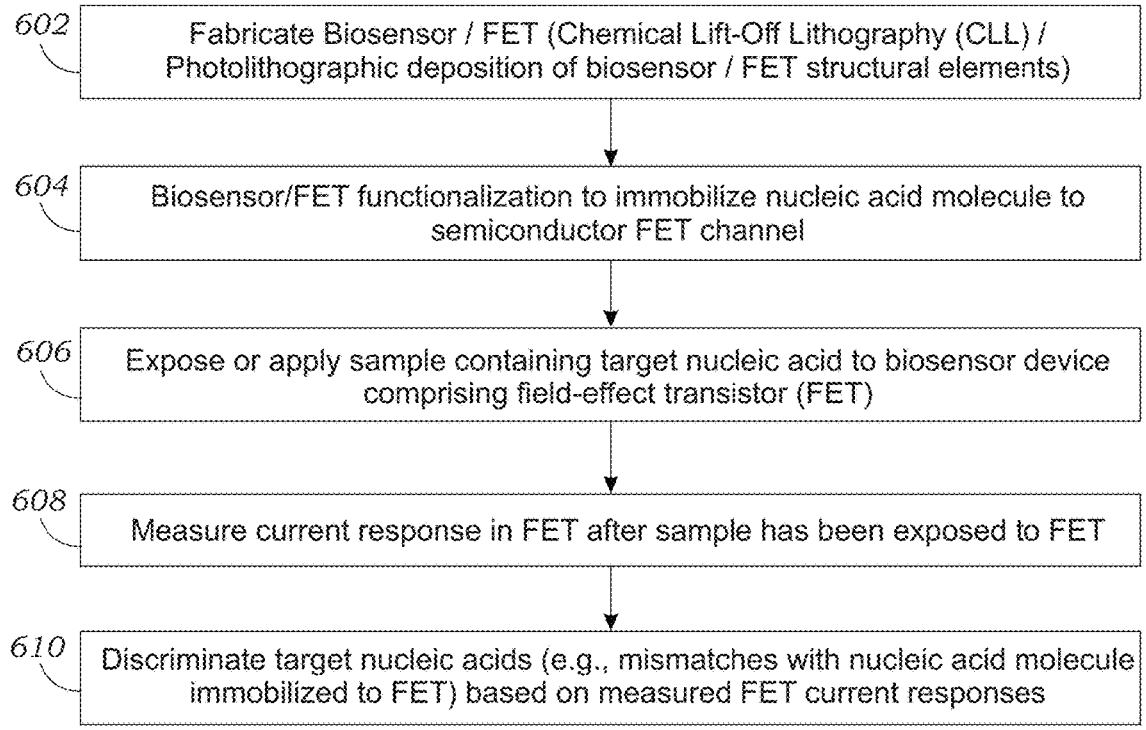
FIG. 6 is a flow diagram of a further embodiment of FET-based target nucleic acid molecule discrimination.

Referring to FIG. 5, in another method 500, detecting whether a target sequence 142 is complementary or mismatched (or non-complementary) with an immobilized sequence 140 involves fabrication of biosensor device including FET 110 at 502 and functionalization thereof by immobilization sequence 140 at 504, followed by steps 506-510 as described above with reference to FIG. 3. Similarly, referring to FIG. 6, other embodiments of methods 600 for distinguishing or discriminating target sequences 142 (e.g., distinguishing target sequence 142 mismatches with immobilized sequence 140 that functionalizes FET 110) involve fabrication of biosensor device including FET 110 at 602 and functionalization thereof at 604 (followed by steps 606-610 as described above with reference to FIG. 4. Further aspects of FET 110 structure, fabrication, functionalization and operation to implement FET-based detection and discrimination embodiments are described with further reference to FIGS. 7A-11B.

Figure 7A:
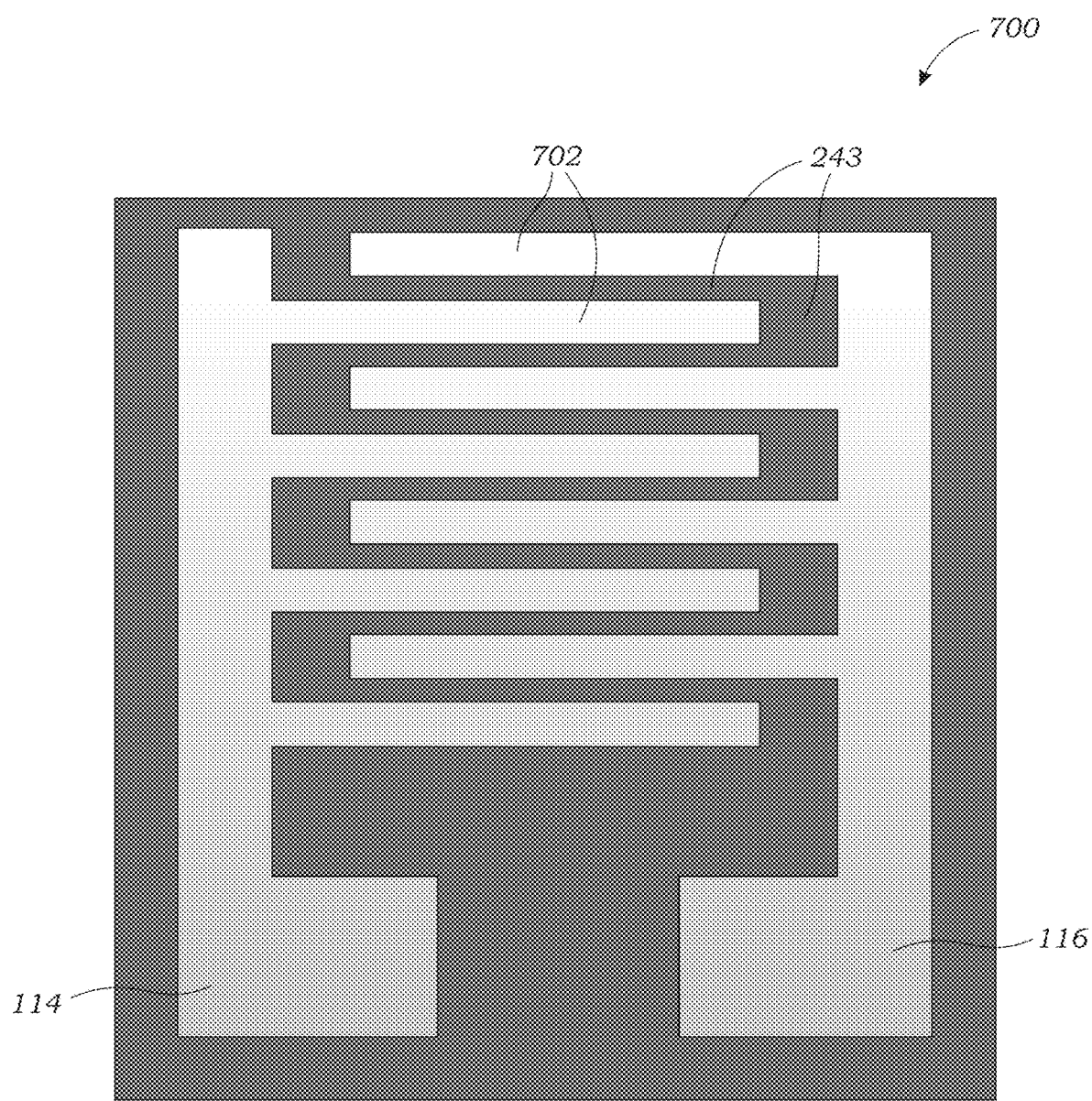
Figure 7B:
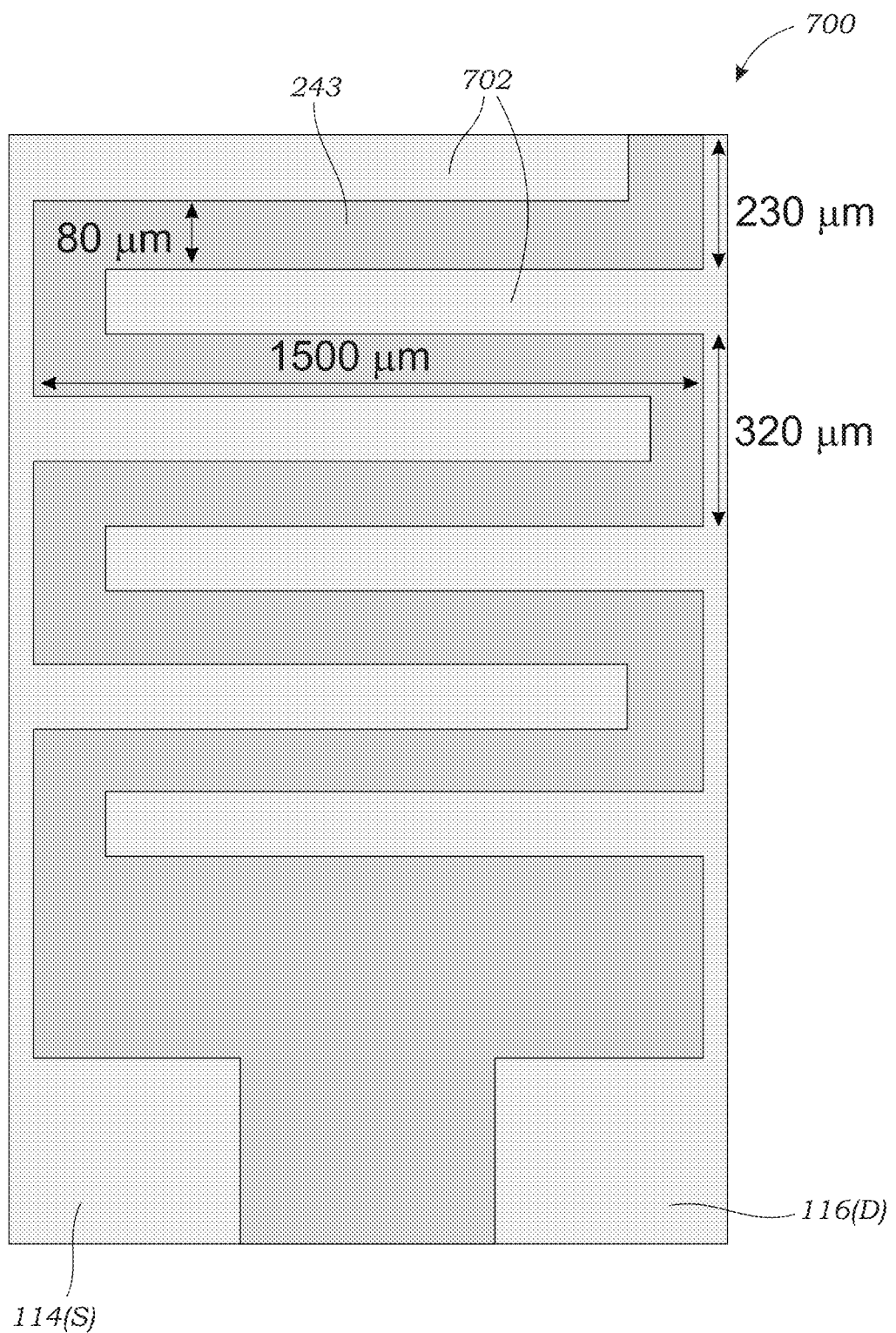
Figure 7C:
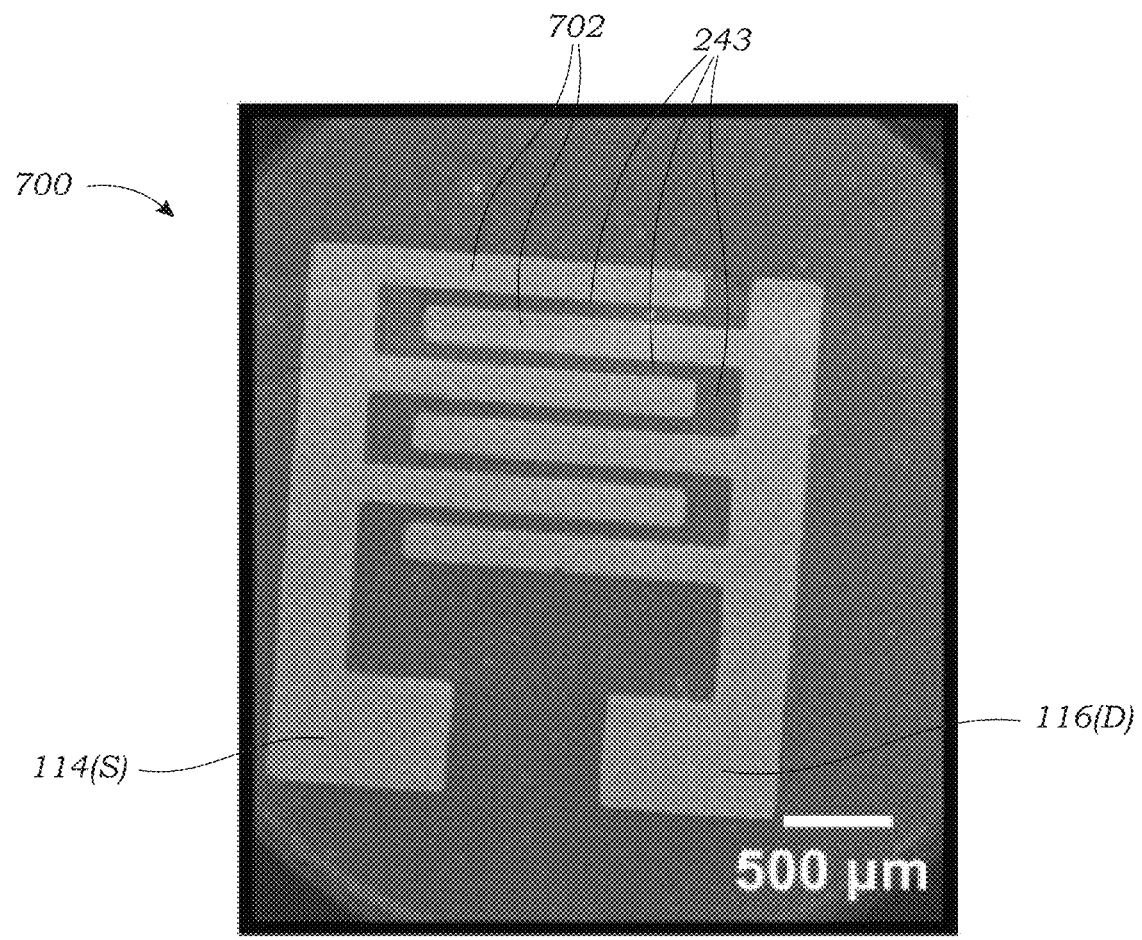

FIGS. 7A-7C illustrate a FET 110 constructed according to one or more embodiments for use as or part of a biosensor device. Biosensor device may include one or more FETs 110 located on a surface or substrate 245. Each FET 110 includes gate electrode 112, source electrode 114 and drain electrode 116, with the gate electrode 112 being in contact with liquid sample 141 containing target sequence 142 being analyzed. Gate electrode 112 may also be provided in a solid-state surface configuration.

FET 110 constructed according to one embodiment includes a gold (Au) source electrode 114 and gold (Au) drain electrode 116 that are formed on substrate 245. Source and drain electrodes 114, 116 are structured to form define an interdigitated array 700 of "fingers" 702. FIGS. 7A-7C illustrate fingers 702 that interleave with one another to define respective narrow semiconductor channel regions 243 (generally, channel 243). One or more immobilized sequences 140 are tethered to channel 243 to functionalize FET 110. According to one embodiment, semiconductor channel region 243 is formed from a thin layer of indium oxide ($In_2O_3$) although it should be appreciated that in other embodiments, different semiconductor metal oxides may be used. According to one embodiment, thin layer of indium oxide has a thickness that is less than about 5 nm (e.g., about 3-4 nm). Generally, a thinner layer increases the sensitivity of the FET 110. In the embodiment illustrated and annotated in FIG. 7B, adjacent interdigitated fingers 702 are separated by a distance of less than about 100 µm, e.g., about 80 µm as shown in FIG. 7B, and extend in the orthogonal direction for about 1,500 µm. FIG. 7B further illustrates the combination of one finger 702 and one channel 243 may extend for about 230 μm and a combination of two indium oxide channel 243 sections and one finger 702 may extend for about 320 μm. It will be understood that the exemplary interdigitated array 700 configuration and dimensions are provided as non-limiting examples of how FET 110 may be structured. Further structural, fabrication, functionalization and operation details are described in further detail below with reference to FIGS. 8A-11B.

Figure 8A:
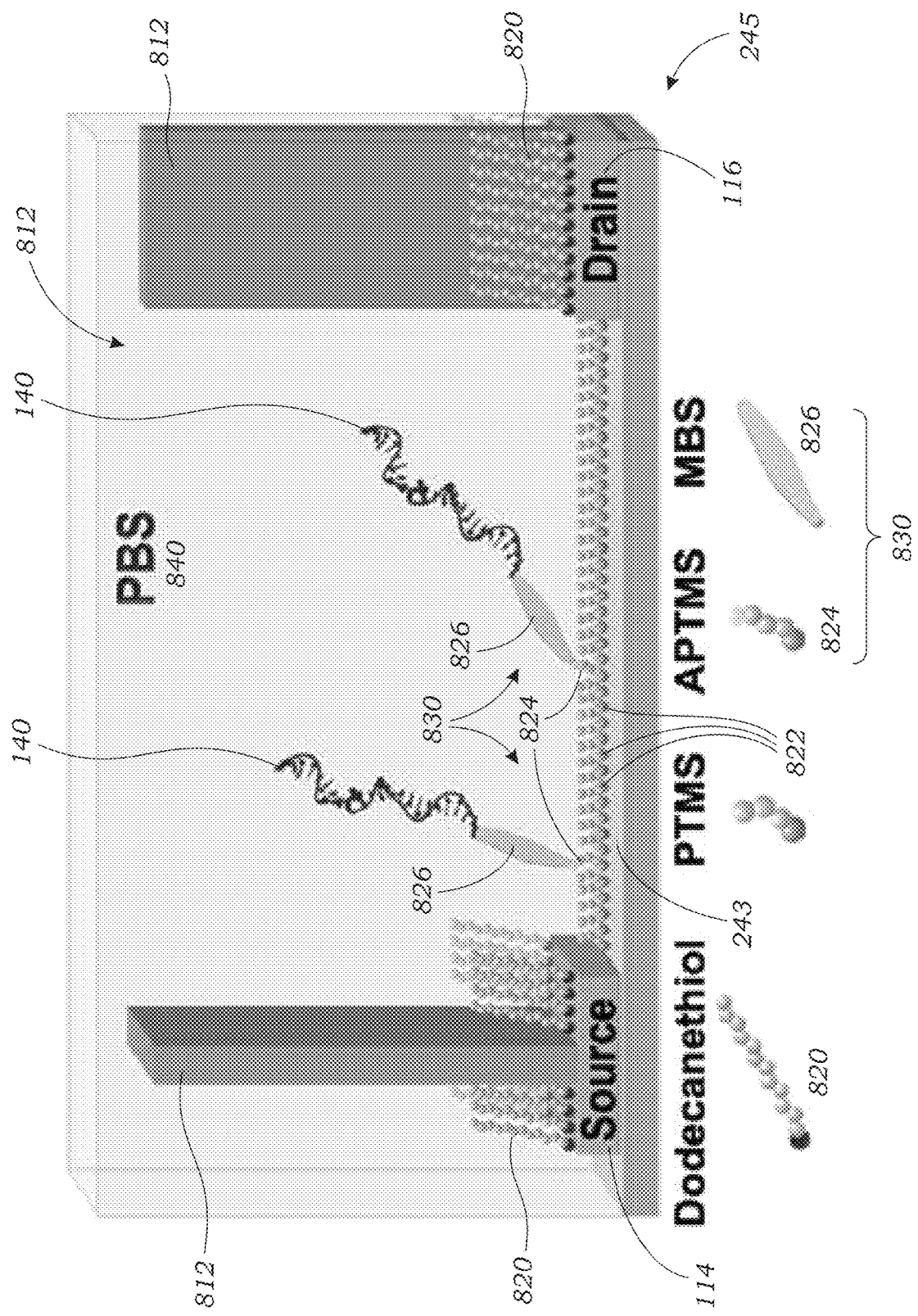
FIG. 8A schematically illustrates functionalization chemistry used to indirectly tether or link a nucleic acid to a semiconducting surface or channel of a FET.
Figure 8B:
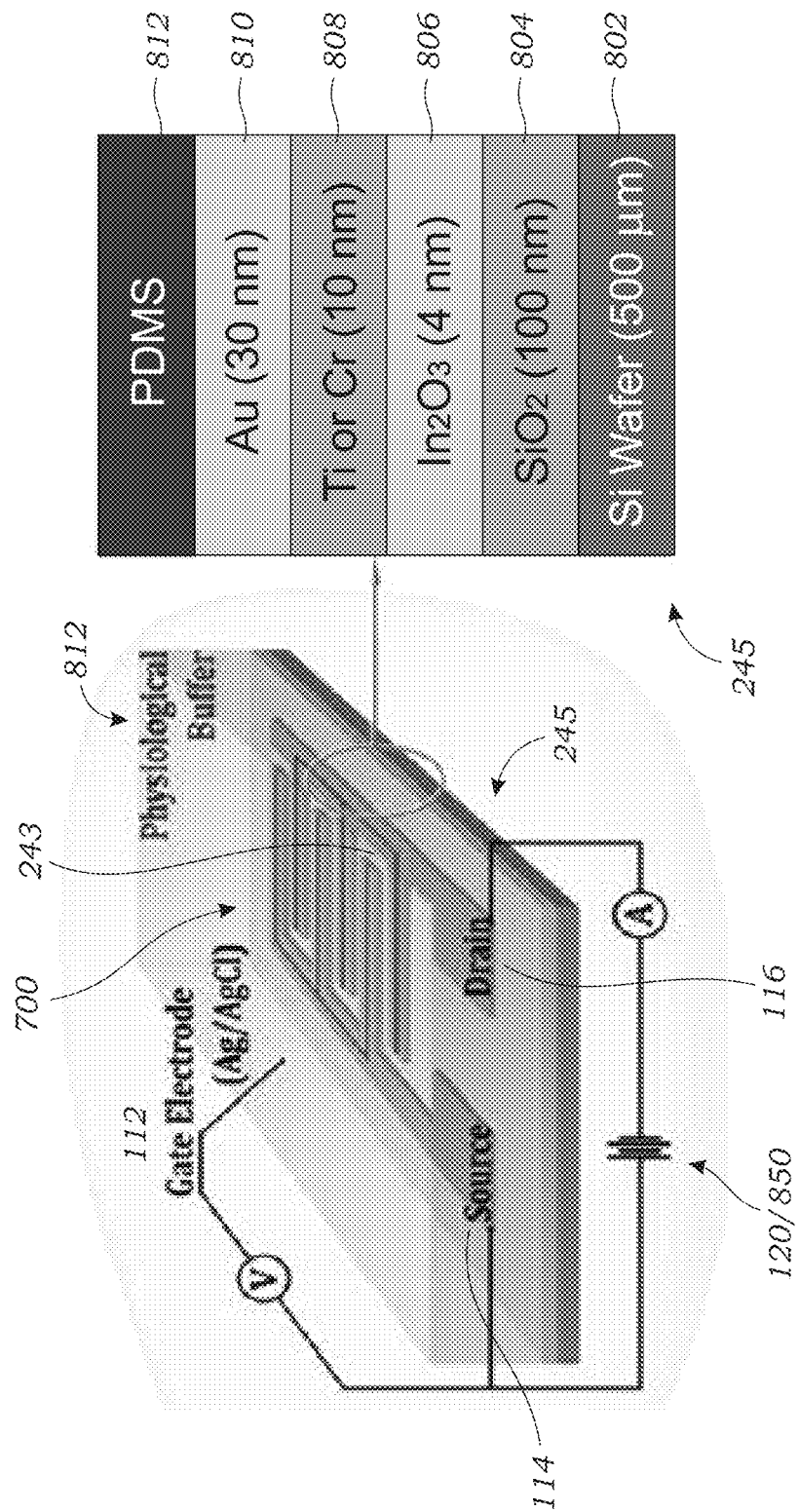
FIG. 8B schematically illustrates a liquid gate FET configuration and cross-sectional FET layers.

Referring to FIGS. 8A-8B, FET 110 is formed on substrate 245 that is made from a silicon (Si) wafer 802 (FIG. 8B) which, in the illustrated embodiment, may be about 500 μm in thickness. In one embodiment, chemical lift-off lithography (CLL) may be used to pattern gold (Au) source electrode 114 and gold (Au) drain electrode 116 on a heavily doped silicon (Si) wafer 802 covered with thermally grown silicon dioxide ($SiO_2$) layer 804 having a thickness of about 100 nm. In the illustrated embodiment, channel 243 is an indium oxide channel 806 and may be formed by aqueous solutions of varying indium(III) nitrate hydrate (99.999%) concentrations being spin-coated onto substrate(s) 802/804 (generally, substrate 254) at 3000 rpm for about 30 seconds. Substrate 254 is then prebaked at about 100° C. for about 5 minutes followed by thermal annealing at about 250° C. for about 1 hour. Indium oxide 806 and gold thin films 810 are deposited successively by spin-coating and electron-beam evaporation, respectively, and CLL may be performed to pattern source and drain electrodes 114, 116.

For CLL-based processes, thin Au films 810 (typically about 50 nm in thickness) are deposited on target substrates by electron-beam evaporation (CHA Industries, Fremont, CA) with Ti or Cr adhesion layers 808 (about 5-10 nm in thickness). To deposit self-assembled monolayers (SAMs) on Au surfaces 810, substrates are immersed in 1 mM ethanolic solutions of 11-mercapto-1-undecanol and incubated overnight. Polydimethylsiloxane (PDMS) stamps with defined patterns are prepared over masters fabricated by standard photolithography or electron-beam lithography. PDMS stamps are exposed to oxygen plasma (e.g., using a source from Harrick Plasma, Ithaca, NY) at a power of about 18 W and an oxygen pressure of about 10 psi for about 40 seconds to yield fully hydrophilic reactive surfaces and are brought into conformal contact with the SAM-modified Au surfaces 810. After about 1 hour, PDMS stamps are carefully removed from the substrates 245, and an aqueous solution of 20 mM iron nitrate and 30 mM thiourea is applied to substrates to etch Au films 810 selectively from the area where the SAM was removed. Ti 808 is removed from the exposed area using a 1:2 (v/v) solution of ammonium hydroxide and hydrogen peroxide. Substrates 245 are rinsed with deionized water and dried under nitrogen before use.

After CLL is used to pattern interdigitated gold 810 source and drain electrodes 114, 116 atop indium oxide layer 806 deposited onto $SiO_2$/Si substrate 802/804 (generally substrate 245), substrate 245 can be briefly exposed to oxygen plasma to remove the hydroxyl-terminated alkanethiols from gold 810 surface, followed by incubation in a 1 mM ethanolic solution of 1-dodecanethiol for 1 h. Additional details regarding the CLL process may be found in Kim, J., Rim, Y. S., Chen, H., Cao, H. H., Nakatsuka, N., Hinton, H. L., Zhao, C., Andrews, A. M., Yang, Y., Weiss, P. S. Fabrication of High-Performance Ultrathin $In_2O_3$ Film Field-Effect Transistors and Biosensors Using Chemical Lift-Off Lithography. ACS Nano 9, 4572-4582 (2015), the contents of which are incorporated by reference herein.

As an alternative to CLL-based fabrication methods used to pattern the gold (Au) source and drain electrodes 810/114, 810/116 described above, sequential deposition processes may be used. In this fabrication process, indium oxide 806 precursor is spin-coated on substrates 245 at about 3000 rpm for about 30 seconds. As-spun films are then prebaked at about 100° C. for about 1 minute followed by thermal annealing at about 350° C. for about 3 hours. Titanium (Ti) 808 and gold (Au) 810 of respective thicknesses of about 10 nm and about 30 nm are deposited sequentially using an e-beam evaporator through the shadow mask to form interdigitated source and drain electrodes 114, 116. Gold (Au) source electrode 810/114 and gold (Au) drain electrode 810/116 are typically passivated with high-quality self-assembled monolayers (e.g., dodecanthiol 820) to prevent functionalization of source and drain electrodes 114, 116 with thiolated (HS) DNA or other nucleic acids.

While CLL and photolithographic methods are described being used to fabricate FET 110 structures, other semiconductor materials and fabrication methods can also be used in embodiments.

Continuing with reference to FIGS. 8A-8B, after thorough rinsing with ethanol, intermediate linking element 830 is formed. Intermediate linking element 830 serves to tether or immobilize nucleic acid molecule or sequence 140 to thin indium oxide channel 243. FIGS. 8A-8B schematically illustrates one embodiment of functionalization chemistry that is used to tether or immobilize nucleic acids (DNA/RNA) 140 to semiconductor surfaces and a spacer 822 that separates intermediate linking elements 830 used to immobilize the nucleic acid to indium oxide channel 243 surface.

In the illustrated embodiment, intermediate linking element 830 is a multi-component intermediate linking element and includes a (3-aminopropyl)trimethoxysilane (APTMS) component 824 and a 3-maleimidobenzoic acid N-hydroxysuccinimide ester (MBS) component 826. In the illustrated embodiment, APTMS 824 links to or is tethered to indium oxide channel 243, MBS 826 is linked or tethered to APTMS 824, and nucleic acid molecule or sequence 140 is immobilized (indirectly) to indium oxide channel 243 via intermediate linking element 830, i.e., via APTMS 824 and MBS 826 components of intermediate linking element 830.

To anchor or immobilize nucleic acid molecule or sequence 140 (e.g., deoxyribonucleic acid (DNA)) to channel 243, substrate 245 is rinsed with deionized water immersed in about 1 μM solution of thiolated (HS) single stranded DNA in 1× Phosphate Buffered Saline (PBS) 840 for about 1 hour, rinsed again with deionized water and blown dry with nitrogen. While conventional silane chemistry is described herein as the method of immobilizing nucleic acid molecule or sequence 140 to indium oxide layer/channel 243, it should be appreciated that reactively functionalized nucleic acids 140 may be immobilized to channel 243 using other surface chemistries known to those skilled in the art.

According to one embodiment, it is preferable to have the linking chemical functionality 830 be as short as possible so that charge redistribution associated with hybridization occurs close to the semiconductor channel 243 surfaces. In experiments described herein, single stranded DNA 140 was immobilized to indium oxide channel 243 regions. It should be appreciated, however, that in other embodiments, single stranded ribonucleic acid (RNA) 140 may be immobilized to the indium oxide channel 243 region (e.g., to detect RNA-RNA duplexes). In other embodiments, a morpholino oligomer 140 may be immobilized to indium oxide channel 243 region.

A spacer element in the form of trimethoxy(propyl)silane (PTMS) 822 (e.g., 1 to 9 volume/volume (v/v) ratio) is thermally evaporated to indium oxide 806 surface at about 40° C. for about 1 hour, and substrate 245 is immersed in a about 1 mM solution of 3-maleimidobenzoic acid N-hydroxysuccinimide ester (MBS) 826 dissolved in 1 to 9 volume/volume (v/v) mixture of dimethyl sulfoxide and 1×PBS 840 for about 30 min. As shown in FIG. 8A, spacer element 822 is passive in that no intermediate linking element 830 or target nucleic acid molecule or sequence 842 is tethered thereto. Spacer elements are laterally disposed between respective intermediate linking elements 830 (824/826) to separate respective linking elements 830. For these purposes, a ratio of APTMS 824 of intermediate linking element 830 to passive spacer element PTMS 822 is less than about 1 to 9. These ratios ensure that the active component APTMS 824 is deposited in moderation and that excessive target nucleic acid molecules 142 are not tethered to respective immobilized nucleic acid molecules 141, which may sterically interfere with one another and/or alter current responses 130 and determinations based on same. Dodecanethiol 820 is used to passivate source and drain electrodes 114, 116. It will be understood that embodiments described above are not so limited.

FIG. 8B illustrates a schematic representation of a biosensor containing a single FET 110. Also illustrated is the external off-chip circuitry 850 or analyzer 120 components used to measure changes in transconductance (current response) that are measured in response to hybridization of target nucleic acids or sequences 142 with immobilized nucleic acids or sequences 140 in semiconductor channel region 243 of FET 110. As a particular example, single-stranded target DNA or RNA 142 is detected via charge redistribution that occurs upon hybridization with complementary oligomers surface-tethered or immobilized 140 to one or more FETs 110. Hybridization-induced rearrangements of nucleic-acids gate the transconductance of semiconductor channels 243. When occurring in close proximity to channels 243, this gating effect is sensitive to differences in charge rearrangements associated with even single nucleotide base-pair mismatch 250 (e.g., C-T, C-A, C-C mismatch) in complementary nucleic acids.

In one embodiment, (3-aminopropyl)trimethoxysilane (APTMS) 824 and trimethoxy(propyl)silane (PTMS) 822 (e.g., in a 1 to 9 volume/volume (v/v) ratio except where otherwise stated) was thermally evaporated using vapor-phase deposition onto $In_2O_3$ surfaces 806 at about 40° C. for about one hour followed by incubation in about 1 mM ethanolic solutions of 1-dodecanethiol for about one hour to passivate gold (Au) source and drain electrodes 114, 116. In addition to source and drain electrode 114, 116 passivation, this may also reduce or prevent device-to-device cross-talk with other FETs as a result of isolating each device individually during measurements via PDMS cups or wells 812. The cups or wells 812 are used to defined a sample holding region that exposes the liquid sample to the FETs 110. In some embodiments, each FET may have its own cups or wells 812 while in other embodiments the sample may be exposed to multiple FETs 110. Furthermore, substrates 245 have substantial inter-FET distances (~2 mm). Substrates 245 were rinsed in ethanol and immersed in about 1 mM solutions of 3-maleimidobenzoic acid N-hydroxysuccinimide ester (MBS) 826 dissolved in a 1:9 volume/volume (v/v) mixture of dimethyl sulfoxide and PBS 840 for about 30 minutes. MBS 826 crosslinks amine-terminated silanes to thiolated (HS) DNA 140. Immobilization sequence 140 in the form of thiolated (HS) DNA 140 was prepared for attachment to substrates 245 by heating for about 5 minutes at about 95° C. in nuclease-free water and then cooling to room temperature. Substrates 245 were rinsed with deionized water and immersed in 1 μM solutions of thiolated DNA 140 overnight (~18 h), rinsed again with deionized water, and blown dry with $N_2$ gas.

According to one embodiment, in order to maximize channel 243 surface-to-volume ratios, FETs 110 were fabricated with ultrathin (~4 nm) indium oxide semiconductor films 806. Aqueous solutions of indium(III) nitrate hydrate $(In(NO_3)_3 \cdot xH_2O, 99.999\%)$ were spin-coated at about 3000 rpm for about 30 seconds onto heavily doped silicon wafers 804 (University Wafer, Boston, MA or WaferPro, San Jose, CA) each having about a 100 nm-thick thermally grown $SiO_2$ layer. Substrates 245 were prebaked at about 150° C. for about 10 minutes followed by thermal annealing at about 350° C. for about 3 hours. Interdigitated 700 source and drain electrodes 114, 116 (e.g., 1500 μm length, 80 μm width, 10 nm Ti, 30 nm Au) as shown in FIG. 7B were patterned by standard photolithography and deposited by electron-beam evaporation on top of indium oxide to obtain large transconductances and uniform current distributions.

In experiments described herein, multiple single stranded DNA oligomers 140 (or RNA) were immobilized to indium oxide channel 243 regions although it should be appreciated that it may be possible for FET 110 to function with only a single nucleic acid molecule 140 being bound to channel 243 region depending on FET 110 sensitivity. In some alternative embodiments, each FET 110 that is located on biosensor device may have a different immobilized nucleic acid 140. For example, a biosensor device may contain a plurality of FETs 110 with different FETs 110 having different immobilized nucleic acid molecules immobilized on different FETs 110. This permits multiplex testing of a sample for a number of different nucleic acid target sequences 142 using a single biosensor device. Of course, in other embodiments, the same immobilized nucleic acid 140 may be used for multiple different FETs 110 contained in a single biosensor device. Having described how FETs 110 may be fabricated and functionalized according to embodiments, current responses 130 of same for detection and/or discrimination of target molecules or sequences 142 are described in further detail with reference to FIGS. 9A-11B.

As described above with reference to FIG. 1, changes in transconductance of FET 110 resulting from nucleic acid or sequence 140/142 hybridization are measured by a semiconductor parameter analyzer 120. During operation, source electrode 114 and drain electrode 116 are held at a constant voltage (e.g., ~10 mV) while gate electrode 112 voltage is swept (e.g., between 0 and 400 mV in 5 mV steps for a sweep time of several seconds (e.g., 4-5 seconds) and typically less than 10 seconds. Current response 130 (between source and drain electrodes 114, 116) is measured by analyzer 120 in response to changing gate electrode 112 voltage.

In one embodiment, measured current response 130 in FET 110 is performed by measuring how the source electrode 114—drain electrode 116 current changes in response to the presence of target nucleic acids 142. That is to say, an I-V (current-voltage) curve is obtained after the liquid sample 141 has been exposed to FET 110 for a certain period of time (e.g., after several minutes). For example, the I-V measurements may be obtained every several minutes. Additional measurements are made as time progresses (e.g., every 5 minutes or so) with current shifts typically being observed between about 30 and 60 minutes after sample addition. Typically, at least 20 minutes or so is needed after sample addition to the FET 110 to indicate whether a target nucleic acid 142 is complementary, a mismatch or noncomplementary relative to a nucleic acid immobilized 140 to the thin semiconductor material 243 of the FET 110.

Another I-V curve is obtained for sample that is free of target nucleic acids 142 so that the shift in current 130 can be observed in response to hybridization of immobilized nucleic acid 140 tethered to channel 243 and target nucleic acids 142. The current response or shift 130 at one or more particular voltages may be used to detect and/or discriminate between hybridization of complementary nucleic acid sequences and mismatched nucleic acid sequences. In this regard, it has generally been found that complementary nucleic acid binding events (e.g., as depicted in FIG. 2B) produce larger current shifts 130 as compared to binding events from mismatched 250 nucleic acids (as depicted in FIG. 2C).

As described with reference to FIGS. 1, 2A-D, 9A-9B, FET-based biosensor device contains immobilized sequence 140 in the form of single stranded DNA 140 in the semiconductor channel region 243, and FIGS. 2B-2D depict three different modes of operation: 1. FET 110 is hybridized with a target sequence 142c of complementary DNA (FIG. 9B) or RNA, 2. FET 110 is hybridized with target sequence 142m of DNA (FIG. 9B) or RNA that contains single-base mismatches 250, and 3. FET 110 is hybridized with target sequence 142nc of non-complementary DNA (FIG. 9B) or RNA. Each mode of operation produces a different measured current response 130 in response to sweeping voltage at gate electrode 112 and each base pair mismatch 250 also results in a different current response 130. The comparison of parallel measurements from a multiplicity of FETs 110 can also provide additional information.

Experiments were conducted using the FET-based biosensor device to detect and discriminate between complementary and mismatched DNA and RNA sequences, and results are illustrated in FIGS. 9A-9D (involving immobilized DNA molecule 140 and DNA target molecule or sequence 142) and 10A-10B (involving immobilized DNA molecule 140 and RNA target molecule or sequence 142).

All electronic measurements were done in 0.1× phosphate-buffered-saline (PBS 840, pH 7.4) as the liquid gate electrode 112. The tested FET-based sensor used a small polydimethylsiloxane (PDMS) cup or well 812 (as depicted in FIGS. 8A-8B) that was used to contain the PBS solution 840 to a single FET 110. For these measurements, a gate bias ($V_{GS}$) was applied through a Ag/AgCl reference electrode (0-400 mV) that touched the PBS solution 840, and source electrode 114—drain electrode 116 current ($I_{DS}$) was measured through the interdigitated gold electrodes. The measurements were performed on a probe equipped with a Keithley 4200A-SCS semiconductor parameter analyzer 120.

To use the FET-based biosensor, sample 141 is exposed or applied to FET 110. For example, the sample may be loaded into a well (e.g., PDMS well 812) that surrounds the active region of FET 110. The sample 141 may include a biological fluid such as blood, urine, saliva, or the like. In some embodiments, the bodily fluid may be a non-diluted physiological sample. Alternatively, the sample 141 may be diluted with an appropriate buffer solution or water. Alternatively, the FET-based biosensor may be integrated into a device that is directly placed into contact with a bodily fluid of a subject. Notably, the FET-based device described herein is able to detect and/or discriminate between mismatched and complementary nucleic acid sequences 142 at high (e.g., physiological) concentrations. This is attributed to the unique steric and conformational changes that are associated with nucleic acid binding between the target nucleic acids and the immobilized single stranded nucleic acids on the FET device. The parameter analyzer can then be used to monitor changes in transconductance as measured by current responses. This may be done in real time or, alternatively, after several minutes of incubation.

First, current-voltage ($I_{DS}$-$V_{GS}$) characteristics were measured for FETs 110 with only PBS buffer 840. Then, a solution 141 of the DNA/RNA (0.1×PBS) was introduced into the buffer solution for a total DNA/RNA concentration of 1 µM. $I_{DS}$-$V_{GS}$ characteristics of FETs 110 were measured again after 30 min of DNA/RNA incubation, and these measured differences in response were used to generate current response data 130 shown in FIGS. 9A, 9C, 9E-G and 10A. For all RNA measurements (for FIGS. 10A-10B), nuclease-free reagents and materials were used.

Figures 9A, 9B:
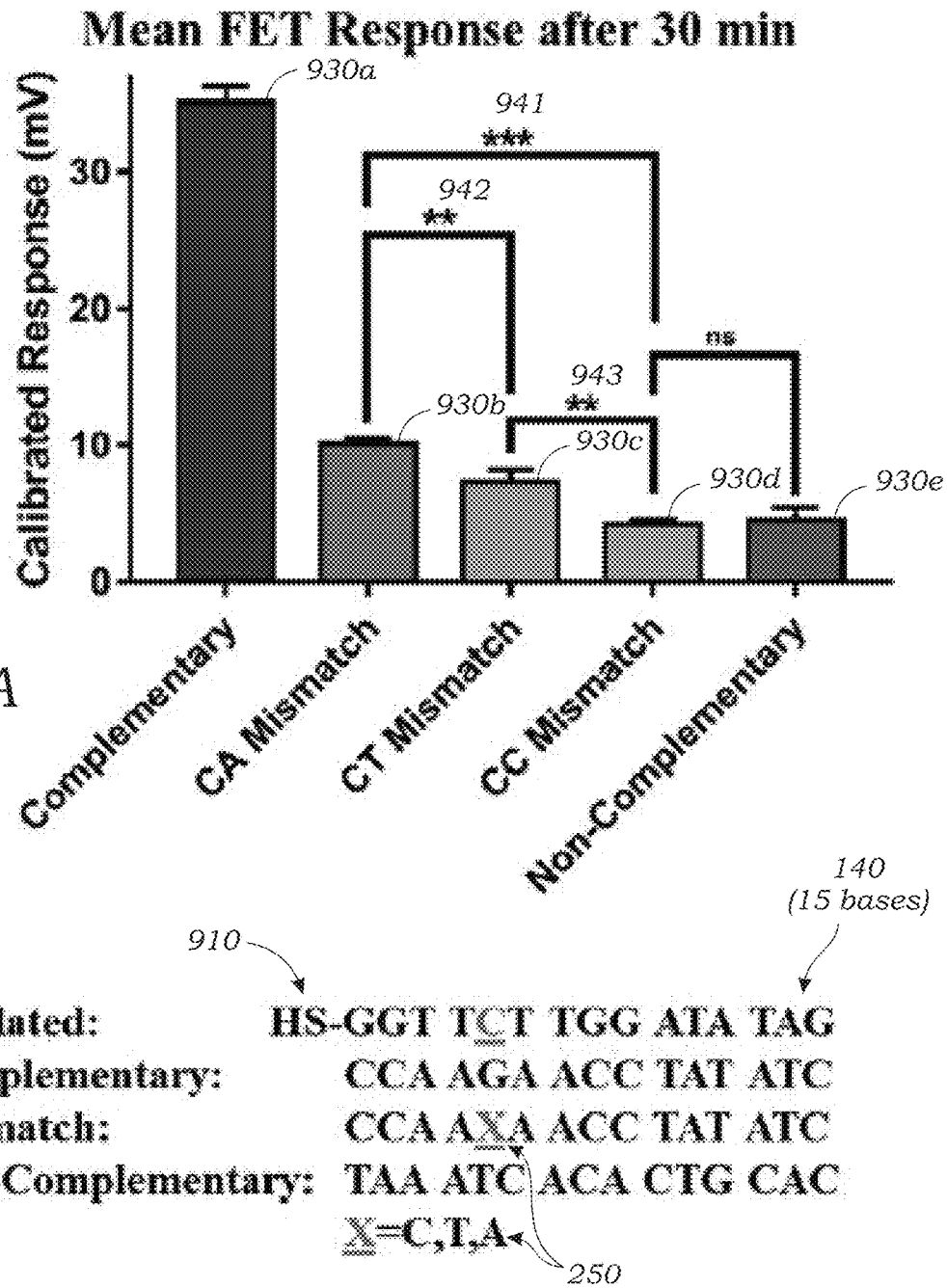

Referring to FIGS. 9A-9B, FET 110 was functionalized with nucleic acid molecule or sequence that was thiolated (HS) to bind to second linking component (MBS 826 in FIG. 8A) to indirectly immobilize nucleic acid molecule or sequence 140 to indium oxide channel 243.

FIG. 9A illustrates results of an experiment performed using the FET-based biosensor that contained a fifteen (15) base pair DNA oligonucleotide 140 (shown in FIG. 9B) that was thiolated (HS) and immobilized on semiconductor channel 243 of FET 110 via intermediate linking member 830 as shown and described above with reference to FIG. 8A. FIG. 9B also illustrates examples of 15 base pair target sequences that were complementary 142c ("c" referring to complementary), mismatch 142m ("m" referring to mismatch) and non-complementary 142nc ("nc" referring to non-complementary).

As shown in FIG. 9B, all of the 15 bases in the immobilized DNA oligonucleotide 140 match respective bases in the complementary target sequence 142c (properly matching G-C and matching A-T). Also as shown in FIG. 9B, the 15 bases in the immobilized DNA oligonucleotide 140 that is a mismatch 142b includes a base "X" which may be "C," "T" or "A" all of which are a mismatch 250 for "C" at the corresponding "X" position in the immobilized DNA oligonucleotide 140. FIG. 9B also provides an example of a non-complementary target sequence 142nc that does not have corresponding matches or substantially no matches to the bases in the immobilized DNA oligonucleotide 140.

FIG. 9A illustrates the mean current response 130 (i.e., shift of $I_{DS}$-$V_{GS}$ characteristics measured in mV at a $V_{GS}$ of 400 mV) that was observed after 30 minutes of incubation with different target DNA sequences 142c, 142m, 142nc. As seen in FIG. 9A, embodiments were able to detect and discriminate single DNA base pair mismatches 250 from fully complementary sequences 142c based on current responses 930a (for complementary) and 930b-d (for mismatch). In the illustrated example, current response 930a for a target sequence 142c that was complementary to immobilized sequence 140 had a current response that was multiple times greater than all of the mismatch current responses 930b-d (for C-A, C-T and C-C mismatches 250) and also multiple times greater than current response 930e for non-complementary target sequence 142nc.

FIG. 9A also illustrates that embodiments were able to discriminate or distinguish target sequences 142 with different types of mismatches 250 given the different current responses 930b and 930d. For example, the difference between the current response 930b for "CA mismatch" and the current response 930d for "CC mismatch" are clearly identifiable due to the current response 930b for CA mismatch being about twice as large as the current response 930d for CC mismatch. Thus, in the illustrated embodiment, embodiments were able to more accurately discriminate or distinguish between C-A and C-C mismatches (*) 941 and also able to accurately discriminate or distinguish C-A mismatch from C-T mismatch () 942 and CT mismatch from CC mismatch (**) 943. Embodiments were also able to discriminate or distinguish C-A and C-T mismatches from non-complementary sequences based on current responses 930c-930e and 930d-930e.

Larger changes in transconductance result from better sequence matches (e.g., complementarity), presumably because the radius of gyration of double-stranded nucleic acids change vs. single-stranded nucleic acids the most in this case. Single mismatches 250 can be differentiated and the changes in transconductance are indicators of the type and position of the mismatch 250 (relative to the transistor gate surface). The sensitivity of the FET 110 biosensor can be optimized by changing the ionic strength of the solution, as the higher the ionic strength, the greater the screening of the charge motion. Salt concentration, temperature, and nucleic acid identity and length can all be used to tune the binding strength of the interactions and thus, the strength of the signal. Sequences that vary at a single base being targeted can be placed on different transistor elements to give better signal-to-noise of notable target DNA or RNA sequence variations.

Figures 9C, 9D:
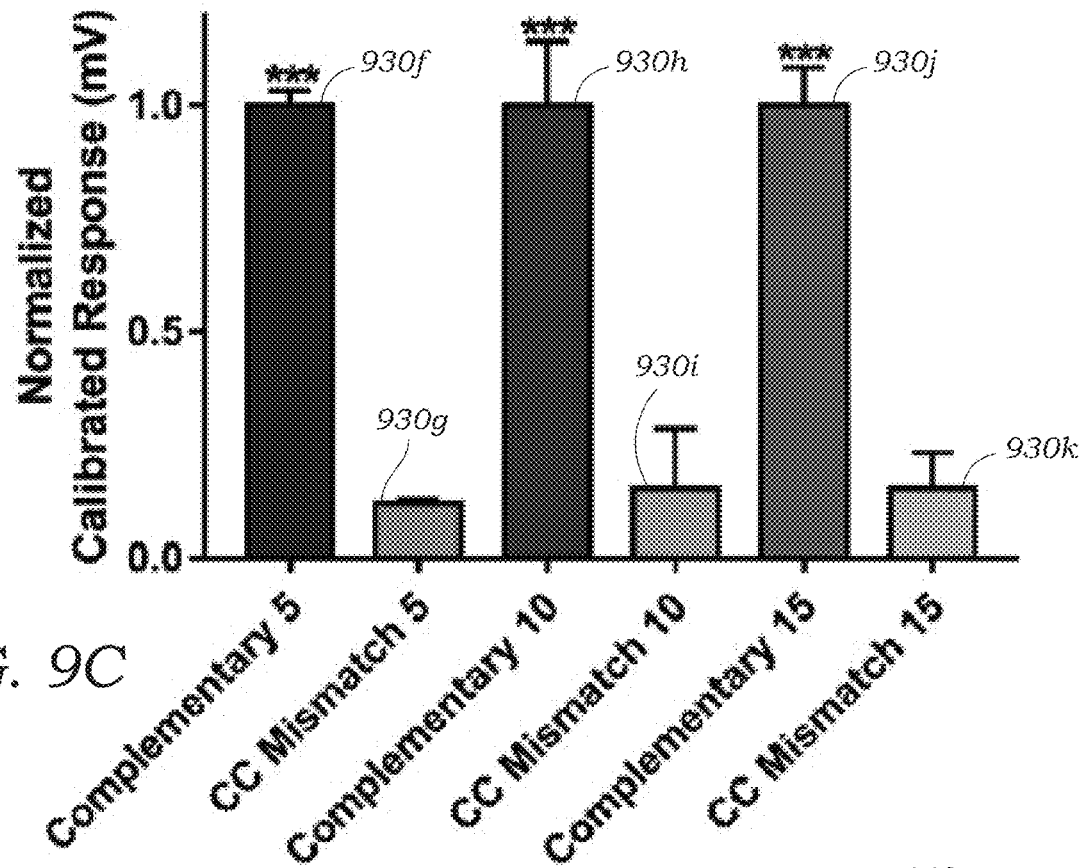

FIG. 9C illustrates the normalized mean response 130 that was observed in response to 30 minutes of incubation with target DNA 142 with CC mismatches 250 located at different base locations away from the thiolate (HS) 910 attachments (complementary thiolated sequences are also illustrated). The six current responses 930f-k for specific sequences 140, 142c, 142m used for the experiment of FIG. 9C are provided in FIG. 9D. The illustrated example demonstrates that CC mismatches 250 at 10 and 15 bases away from the thiolate (HS) attachments 910 can be detected.

FIGS. 9E-9G further illustrate representative transfer characteristics (I-V curves) 130 of DNA functionalized FET 110 over time upon exposure to a fully complementary target sequence 142 (FIG. 9E), a non-complementary target sequence (FIG. 9F), and a mismatched target sequence 142 (FIG. 9G) respectively. Curves for complementary sequences show a stable decrease in current over time 960, whereas curves for non-complementary (FIG. 9F) and mismatched (FIG. 9G) sequences shift back towards the baseline current over time 970. For the mismatch and non-complementary sequences, it is hypothesized that the shift in the beginning is due to the addition of the negatively charged DNA into the solution, resulting in the initial signal. However, what is sensed over time is DNA hybridization, i.e., DNA binding and staying near the surface, which likely occurs to the greatest degree for the complementary sequence. Thus, the signal may be less prominent over time for the complementary and mismatch sequence due to observing reduced or minimal hybridization or binding in those cases.

Figures 10A, 10B:
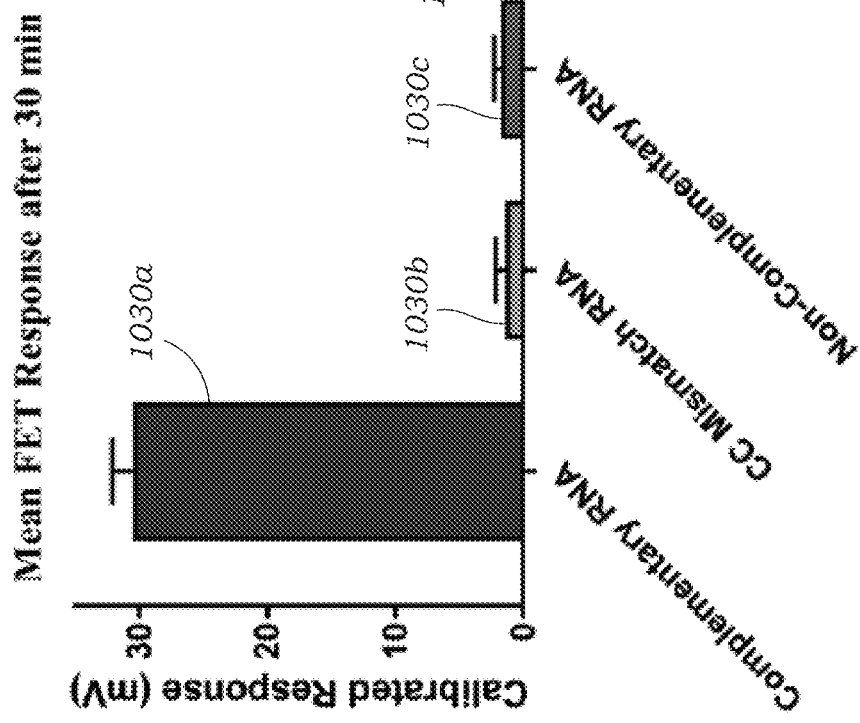
FIG. 10A illustrates mean FET responses, after 30 minutes of target RNA incubation demonstrating that FET devices constructed according to embodiments can be used to detect single nucleotide polymorphisms in RNA.
FIG. 10B illustrates DNA and RNA sequences used for experiments shown in FIG. 10B.

While certain embodiments have been described with reference to target sequence 142 in the form of a target DNA sequence, FIGS. 10A-10B illustrate that embodiments are also able to effectively detect and/or discriminate other target sequences including target RNA sequences and determine whether target RNA sequences are complementary 142rc ("r" referring to RNA and "c" referring to complementary), include a base mismatch 142rm ("r" referring to RNA and "m" referring to mismatch) or are non-complementary 142mc ("r" referring to RNA and "nc" referring to non-complementary) relative to an immobilized sequence 140 (e.g., thiolated DNA sequence immobilized to channel 243). Current responses 1030a-c illustrate that complementary target RNA sequences 142 are clearly distinguishable from target RNA sequences that include at least one mismatch 250 or that are non-complementary.

Figures 11A, 11B:
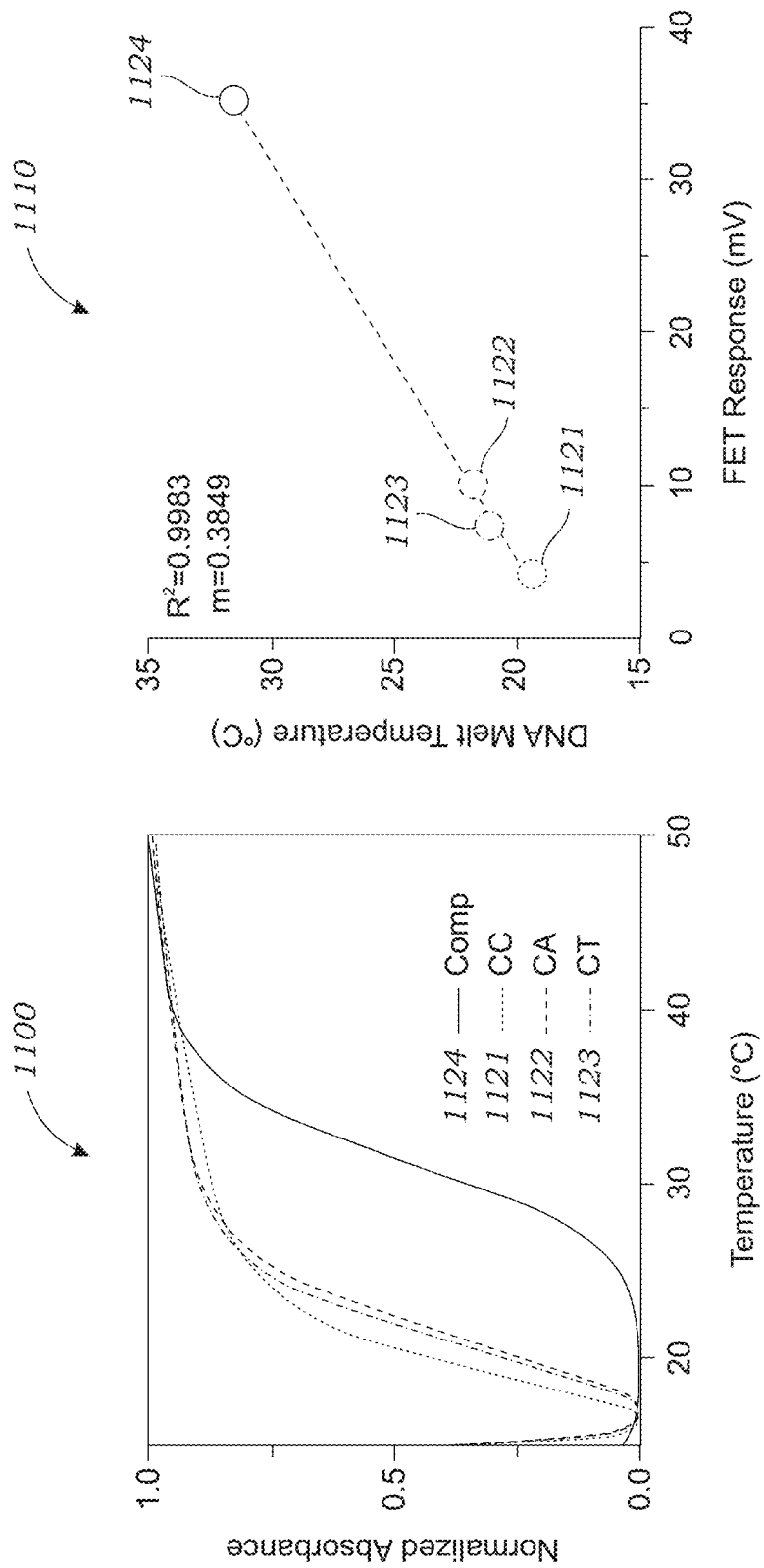
FIGS. 11A-11B are graphs demonstrating effectiveness of results achieved with FET devices constructed according to embodiments relative to DNA melting curves and FET responses relative to DNA melt temperatures.

Experiments summarized in FIGS. 11A-11B further demonstrate validation and effectiveness of embodiments. FIG. 11A is a graph 1100 of a DNA melting curve of sequences listed in FIG. 9B, and FIG. 11B is graph 1110 of correlation analysis of FET 110 current responses 130 to different mismatched sequences (FIG. 9A) versus corresponding melting temperatures with linearity index ($R^2$) and regression slope (m). FIGS. 11A-11B illustrate that FET-based detection and discrimination results of FIG. 11B matched conventional testing using melting curves of DNA as shown in FIG. 11A. To generate melting curves, double stranded DNA is heated and eventually the strands separate and absorbance changes when the strands separate. For double stranded DNA that is strongly held together (like complementary DNA will all base pairs matching), a high temperature is required to break the double helix (solid line) whereas lower temperatures are needed to break strands including mismatches.

Validation of embodiments is also demonstrated in FIG. 11B by higher DNA melting temperatures being required for observed FET responses 130. For example, CC mismatch 1121 has the lowest melting temperature in graph 1100 and also the lowest FET response in graph 1100, and melting temperatures and FET responses 130 correspondingly increase for CA mismatch 1122, CT mismatch 1123, and complementary 1124, which clearly shows the highest melting temperature and corresponding highest FET response 130.

The methods described herein demonstrate the ability of these DNA-functionalized FETs to distinguish between different types, locations, and numbers of SNPs by taking advantage of the differences in stabilities (hybridization) of these SNPs. The detection limit of hybridization of target DNA with the FETs is low and is in the femtomolar concentration range or lower. The method and FET 110 device has been used to detect and discrimination of different types and locations of SNPs on 15-mer DNA. SNPs in RNA sequences may also be detected. The FET 110 can also be used to detect disease-risk-associated SNPs, for example, SNPs in noncoding RNA or wild card bases, which underlie genetic predispositions to cancer.

The method may be used in areas relating to disease diagnostics and precision medicine. Detecting SNPs in oligonucleotides from biological, patient, fixed, and/or biobanked samples, related to a variety of diseases, would be useful for point-of-care and oncology/pathology applications. Label-free electronic nanobiosensors and nanobiosensor arrays could be translated into clinical and clinical laboratory settings. The methods described herein circumvent the need for amplification of DNA/RNA from patient or other samples, saving time and costs, and reducing error rates and bias associated with amplification.

While other FET-based biosensor technologies have been demonstrated, these sensors suffer from shortcomings associated with sensitivity, particularly in physiological fluids, or low throughput in their fabrication. This platform circumvents both of these deficiencies of conventional FET-based biosensors. First, Debye length limitations are circumvented that hinder FET-based biosensing in high ionic strength fluids or tissue by exploiting conformational changes associated with highly negatively charged nucleic acid backbones that undergo spatial rearrangement upon target hybridization. The charge at and near FET gate-surfaces is substantially different post-hybridization. This technology is scalable and compatible with good manufacturing practice (GMP) processes.

While embodiments of the present invention have been shown and described, various modifications may be made without departing from the scope of the present invention. In addition, while various dimensions may be illustrated in the drawings, these dimensions are intended to be illustrative and not limiting. The invention, therefore, should not be limited, except to the following claims, and their equivalents.

What is claimed is:

1. A biosensor device, comprising:
 a field-effect transistor (FET) comprising:
  a substrate,
  a gate electrode,
  a source electrode disposed on the substrate and having an interdigitated array of fingers,
  a drain electrode disposed on the substrate and having an interdigitated array of fingers,
  a semiconducting film forming a channel between the respective interdigitated arrays of fingers of the source electrode and drain electrode, wherein the gate electrode, the source electrode and the drain electrode are configured so that an electric current flows between the source electrode and the drain electrode and through the channel in response to a voltage applied to the gate electrode;
  at least one single stranded nucleic acid molecule indirectly immobilized to the channel through respective intermediate linking element(s);
  passive spacer elements attached to the channel and laterally disposed between the intermediate linking element(s) to separate respective intermediate linking element(s) and the at least one single stranded nucleic acid molecule indirectly immobilized to the channel, wherein the at least one single stranded nucleic acid molecule is not attached to any of the passive spacer elements; and
 an analyzer coupled to the gate electrode, the source electrode, and the drain electrode and configured to measure the transconductance or current response of the FET; and
 a computing device in communication with the analyzer and configured to analyze the transconductance or current response of the FET and output a result of a tested sample containing a target nucleic acid molecule, wherein the result is one of: complementary, mismatch of a single nucleotide base pair, or non-complementary.

2. The biosensor device of claim 1, wherein more passive spacer elements are attached to the channel than intermediate linking element(s).

3. The biosensor device of claim 2, wherein a ratio of intermediate linking element(s) to passive spacer elements is less than about 1.9.

4. The biosensor device of claim 1, wherein the passive spacer elements comprise trimethoxy(propyl)silane (PTMS).

5. The biosensor device of claim 1, further comprising a wall or cup layer extending upwardly from the source electrode and the drain electrode to define a well comprising the FET to contain a solution containing the sample exposed to the FET.

6. The biosensor device of claim 1, the semiconducting film comprising indium oxide.

7. The biosensor device of claim 6, the semiconducting film comprising a layer of indium oxide ($In_2O_3$) having a thickness less than about 5 nm.

8. The biosensor of claim 1, wherein the intermediate linking element comprises (3 aminopropyl) trimethoxysilane (APTMS) and 3-maleimidobenzoic acid N-hydroxysuccinimide ester (MBS) bound to the APTMS.

9. The biosensor of claim 1, wherein the at least one single stranded nucleic acid molecule immobilized to the semiconducting film comprises deoxyribonucleic acid (DNA).

10. The biosensor of claim 1, wherein the at least one single stranded nucleic acid molecule immobilized to the semiconducting film comprises ribonucleic acid (RNA).

11. A method of using a biosensor device, comprising:
 a field-effect transistor (FET) comprising:
  a substrate,
  a gate electrode,
  a source electrode disposed on the substrate and having an interdigitated array of fingers,
  a drain electrode disposed on the substrate and having an interdigitated array of fingers,
  a semiconducting film forming a channel between the respective interdigitated arrays of fingers of the source electrode and drain electrode, wherein the gate electrode, the source electrode and the drain electrode are configured so that an electric current flows between the source electrode and the drain electrode and through the channel in response to a voltage applied to the gate electrode;
  at least one single stranded nucleic acid molecule indirectly immobilized to the channel through respective intermediate linking element(s);
  passive spacer elements attached to the channel and laterally disposed between the intermediate linking element(s) to separate respective intermediate linking element(s) and the at least one single stranded nucleic acid molecule indirectly immobilized to the channel, wherein the at least one single stranded nucleic acid molecule is not attached to any of the passive spacer elements, the method comprising:
 exposing or applying a sample containing a target nucleic acid to the biosensor device;
 measuring a current response in the FET after the sample has been exposed or applied to the FET with an analyzer coupled to the FET; and
 detecting whether the target nucleic acid is complementary, mismatched, or non-complementary with the at least one immobilized single stranded nucleic acid molecule based on the measured current response.

12. The method of claim 11, wherein the target nucleic acid is present in the sample at a femtomolar concentration range or smaller.

13. The method of claim 11, the target nucleic acid comprising a single nucleotide polymorphism with the one or more nucleic acid molecules.

14. The method of claim 11, exposing the sample comprising exposing a sample comprising a non-diluted physiological sample.

15. The method of claim 11, exposing the sample comprising exposing a sample comprising a physiological sample diluted with a buffer solution.

16. A biosensor device, comprising:
 a field-effect transistor (FET) comprising:
  a substrate,
  a gate electrode,
  a source electrode disposed on the substrate and having an interdigitated array of fingers, a drain electrode disposed on the substrate and having an interdigitated array of fingers, a semiconducting film forming a channel between the respective interdigitated arrays of fingers of the source electrode and drain electrode, wherein the gate electrode, the source electrode and the drain electrode are configured so that an electric current flows between the source electrode and the drain electrode and through the channel in response to a voltage applied to the gate electrode;

at least one single stranded RNA molecule indirectly immobilized to the channel through respective intermediate linking element(s); and passive spacer elements attached to the channel and laterally disposed between the intermediate linking element(s) to separate respective intermediate linking element(s) and the at least one single stranded RNA molecule indirectly immobilized to the channel, wherein the at least one single stranded RNA molecule is not attached to any of the passive spacer elements.

17. The biosensor device of claim 16, further comprising an analyzer coupled to the gate electrode, the source electrode, and the drain electrode and configured to measure the transconductance or current response of the FET.

18. The biosensor device of claim 17, further comprising a computing device in communication with the analyzer and configured to analyze the transconductance or current response of the FET and output a result of a tested sample containing a target nucleic acid molecule, wherein the result is one of: complementary, mismatch of a single nucleotide base pair, or non-complementary.

* * * * *